(12) United States Patent
Ishihara et al.

(10) Patent No.: US 7,101,918 B2
(45) Date of Patent: Sep. 5, 2006

(54) HYBRID TYPE ONIUM SALT

(75) Inventors: Masami Ishihara, Kawagoe (JP); Tsuneaki Maesawa, Kawagoe (JP); Yoji Urano, Kawagoe (JP)

(73) Assignee: Wako Pure Chemical Industries, Ltd., Osaka (JP)

(*) Notice: Subject to any disclaimer, the term of this patent is extended or adjusted under 35 U.S.C. 154(b) by 93 days.

(21) Appl. No.: 10/494,481

(22) PCT Filed: Nov. 1, 2002

(86) PCT No.: PCT/JP02/11446

§ 371 (c)(1),
(2), (4) Date: May 3, 2004

(87) PCT Pub. No.: WO03/040090

PCT Pub. Date: May 15, 2003

(65) Prior Publication Data
US 2005/0020710 A1 Jan. 27, 2005

(30) Foreign Application Priority Data
Nov. 6, 2001 (JP) .............................. 2001-340144

(51) Int. Cl.
*C08F 2/50* (2006.01)
*G03F 7/04* (2006.01)
*C03C 381/12* (2006.01)

(52) U.S. Cl. ........................ 522/31; 522/25; 522/170; 522/181; 430/280.1; 430/281.1; 568/18

(58) Field of Classification Search ................. 522/31; 568/18
See application file for complete search history.

(56) References Cited

U.S. PATENT DOCUMENTS

| | | | |
|---|---|---|---|
| 4,058,401 A | 11/1977 | Crivello | |
| 4,173,476 A | 11/1979 | Smith et al. | |
| 4,683,317 A | 7/1987 | Crivello et al. | |
| 4,882,201 A * | 11/1989 | Crivello et al. | 427/515 |
| 5,502,083 A * | 3/1996 | Abe et al. | 522/31 |
| 6,096,794 A * | 8/2000 | Cunningham et al. | 522/12 |
| 6,365,644 B1 * | 4/2002 | Yamamura et al. | 522/168 |
| 6,368,769 B1 | 4/2002 | Ohkawa et al. | |
| 6,841,333 B1 * | 1/2005 | Lamanna et al. | 430/270.1 |

FOREIGN PATENT DOCUMENTS

| | | |
|---|---|---|
| GB | 1 516 351 | 7/1978 |
| GB | 1 516 352 | 7/1978 |
| JP | 2000-186071 | 7/2000 |
| JP | 2001-55374 | 2/2001 |
| JP | 2001-255647 | 9/2001 |

OTHER PUBLICATIONS

Watt et al, "A Novel Photoinitiator of Cationic Polymerization: Preparation and Characterization of Bis[4-(diphenylsulfonio)phenyl]sulfide Bis-Hexafluorophosphate", Journal of Polymer Science vol. 22, 1789-1796, 1984.*

* cited by examiner

*Primary Examiner*—Susan Berman
(74) *Attorney, Agent, or Firm*—Hamre, Schumann, Mueller & Larson, P.C.

(57) ABSTRACT

The present invention relates to a hybrid type onium salt having an iodonium salt and a sulfonium salt in the molecule, Useful, for example, as a cationic type photopolymerization initiator and an acid generator for a chemically amplified resist and provides a hybrid type onium salt shown by the general formula [1]:

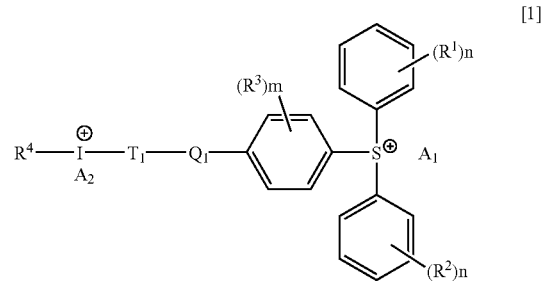

and $R^4$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted or a group shown by the general formula [2]:

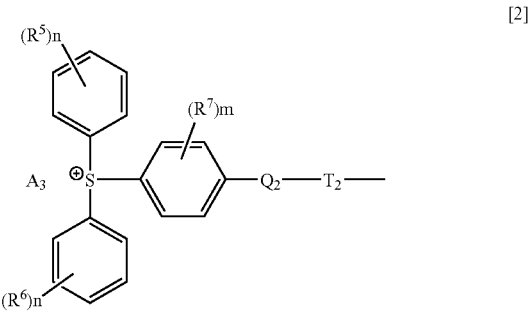

and a polymerization initiator or an acid generator, comprising said onium salt.

32 Claims, No Drawings

HYBRID TYPE ONIUM SALT

TECHNICAL FIELD

The present invention relates to a hybrid type onium salt having an iodonium salt and a sulfonium salt in the molecule, useful as, for example, a cationic type photopolymerization initiator and an acid generator for a chemically amplified resist.

BACKGROUND OF THE INVENTION

A cationic type photopolymerization initiator is widely known as a catalyst for polymerization of, for example, an epoxy compound and a vinyl ether compound, by irradiation with UV, deep UV, electron beams, X-rays, radioactive rays and the like.

As a cationic type photopolymerization initiator, for example, a sulfonium salt such as triallylsulfonium hexafluoroantimonate (see U.S. Pat. No. 4,058,401) or a 4-(phenylthio)phenyldiphenylsulfonium salt compound (see U.S. Pat. No. 4,173,476), an iodonium salt such as diphenyliodonium hexafluorophosphate or diphenyliodonium hexafluoroantimonate (see e.g. JP-A-50-151996, JP-A-60-47029, etc.) and the like are known.

However, these compounds have low acid generation efficiency, and therefore use of them as a cationic photopolymerization initiator makes it difficult to form a polymer with high hardness.

It is also known that a sulfonium salt and an iodonium salt, having, for example, hexafluorophosphate ($PF_6^-$) or tetrafluoroborate ($BF_4^-$) as a counter anion show more remarkably reduced photocuring than those having hexafluoroantimonate ($SbF_6^-$). However, due to strong toxicity of $SbF_6^-$ and probable banning of its use in the future, it is required to study a cation part with a new structure and enhanced photo degradability to develop an onium salt with sufficient curing function even with $PF_6^-$, $BF_4^-$ and the like as a counter anion.

Furthermore, in accordance with the recent trend of higher density integration in semiconductor elements, wavelengths of light sources for irradiation instruments used in fine processing, particularly those used in lithography, become shorter and shorter, and in compliance with this trend, chemically amplified resist compositions, wherein an action of an acid generated from an acid generator as a photo sensitive compound is utilized, have generally been used. Further, a sulfonium salt and an iodonium salt have been used also as an acid generator for these chemically amplified resist compositions.

However, a sulfonium salt and an iodonium salt have low solubility in a solvent for resist such as propylene glycol monomethyl ether acetate (PGMEA) or ethyl lactate, and are hardly dispersed uniformly in a resist. These cause a problem of poor semiconductor device, because the poor solubility not only makes difficult to develop sufficiently high resist sensitivity, but also gives rough profiles or side walls of patterns, resulting in a fall of a resist ingredient forming a pattern on a substrate on etching, or collapsing of a pattern itself, to fail to apply specified etching.

The present invention has been completed under such circumstances as mentioned above, and the theme of the invention is to provide a new hybrid type onium salt having an iodonium salt and a sulfonium salt in the molecule, which can be used more practically as a cationic type photopolymerization initiator and an acid generator for a resist and the like.

SUMMARY OF THE INVENTION

The present invention has been accomplished for the purpose of solving those problems as mentioned above, and provides the following.

(1) A hybrid type onium salt shown by the general formula [1]:

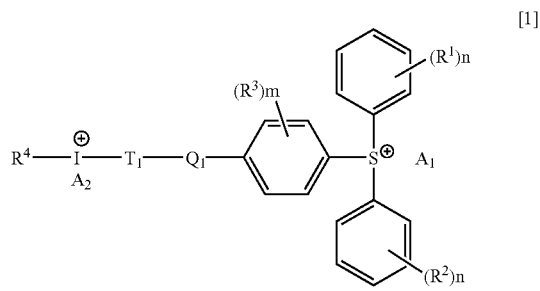

[wherein $R^1$ to $R^3$ are each independently a halogen atom, an alkyl group, a haloalkyl group, an aryl group, an alkoxy group, an aryloxy group, an alkylthio group, an arylthio group or an amino group which may be substituted; $Q_1$ is a direct-linkage, an oxygen atom, a sulfur atom or a lower alkylene chain; $T_1$ is an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted; and $R^4$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, or a group shown by the general formula [2]:

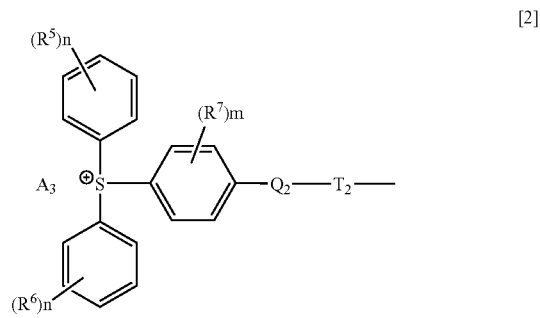

(wherein $R^5$ to $R^7$ are each independently a halogen atom, an alkyl group, a haloalkyl group, an aryl group, an alkoxy group, an aryloxy group, an alkylthio group, an arylthio group or an amino group which maybe substituted; $Q_2$ is a direct-linkage, an oxygen atom, a sulfur atom or a lower alkylene chain; $T_2$ an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted; $A_3$ is a counter anion; m is an integer of 0 to 4; and two ns are each independently an integer of 0 to 5); $A_1$ and $A_2$ are each independently a counter anion; and m and n are the same as described above].

(2) A cationic photopolymerization initiator, which comprises an onium salt shown by the general formula [34]:

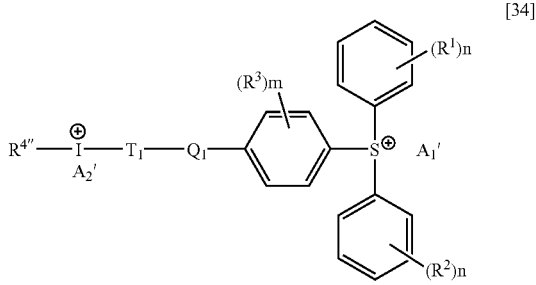

[34]

{wherein $R^{4''}$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, or a group shown by the general formula [35]:

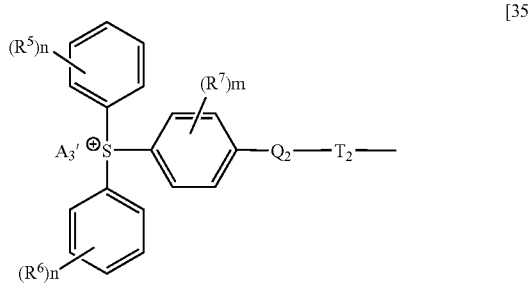

[35]

[wherein $A_3'$ is a counter anion derived from a compound shown by the general formula [7]:

[7]

(wherein $M^1$ is a boron atom or a gallium atom; $R^{11}$ is an aryl group which may have a substituent selected from the group consisting of a lower haloalkyl group, a halogen atom, a nitro group and a cyano group) or an inorganic acid shown by the general formula [10]:

[10]

(wherein $M^2$ is a metalloid atom or a metal atom; and l is an integer of 4 or 6) ; m is an integer of 0 to 4; two ns are each independently an integer of 0 to 5; and $R^5$ to $R^7$, $Q_2$, $T_2$, m and n are the same as described above]; $A_1'$ and $A_2'$ are each independently a compound shown by the above-described general formula [7] or a counter anion derived from an inorganic acid shown by the above-described general formula [10]; and $R^1$ to $R^3$, $Q_1$, $T_1$, m and n are the same as described above}.

(3) A method for polymerizing an α,β-ethylenically unsaturated monomer comprising using said polymerization initiator.

(4) A method for polymerizing a vinyl ether monomer comprising using said polymerization initiator.

(5) A method for polymerizing an epoxy monomer comprising using said polymerization initiator, and (6) An acid generator for a resist, comprising an onium salt shown by the general formula [40]:

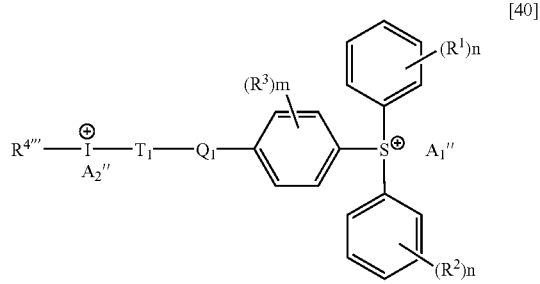

[40]

[wherein $R^{4'''}$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, or a group shown by the general formula [41]:

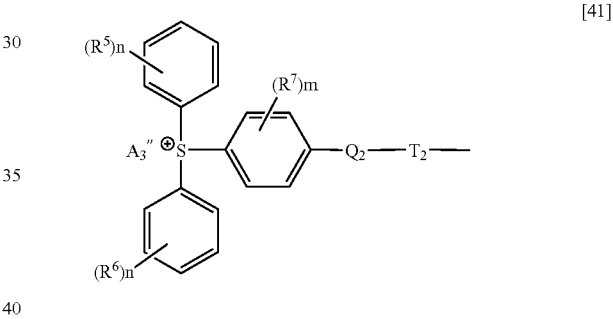

[41]

(wherein $A_3''$ is an anion derived from a compound shown by the general formula [7], an organic acid or an inorganic acid; and $R^5$ to $R^7$, $Q_2$, $T_2$, m and n are the same as described above) ; $A_1''$ and $A_2''$ are each independently an anion derived from a compound shown by the general formula [7], an organic acid or an inorganic acid; and $R^1$ to $R^3$, $Q_1$, $T_1$, m and n are the same as described above].

PREFERRED EMBODIMENTS OF THE INVENTION

The present inventors have conducted extensive study in order to realize the object mentioned above to arrive at the finding that the hybrid type onium salts shown by the above general formulae [1], [34] and [40] are excellent in acid generation efficiency and hence can be a useful cationic type photopolymerization initiator or an acid generator for a resist, without having the problems mentioned above, or raw materials for synthesis thereof, and finally the present invention has been accomplished on the basis of this finding.

In the general formulae [1], [2], [34], [35], [40] and [41], the halogen atom shown by $R^1$ to $R^3$ and $R^5$ to $R^7$ includes, for example, a fluorine atom, a chlorine atom, a bromine atom and an iodine atom.

The alkyl group shown by $R^1$ to $R^3$ and $R^5$ to $R^7$ may be straight chained, branched or cyclic, and includes one having generally 1 to 24 carbon atoms, preferably 1 to 8 carbon atoms and more preferably 1 to 4 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 3-methylpentyl group, a 1,2-dimethylbutyl group, a 2,2-dimethylbutyl group, a 1-ethylbutyl group, a 2-ethylbutyl group, a n-heptyl group, an isoheptyl group, a sec-heptyl group, a tert-heptyl group, a neoheptyl group, a 2-methylhexyl group, a 3-methylhexyl group, a 2,2-dimethylpentyl group, a 3-ethylpentyl group, a 2,4-dimethylpentyl group, a 1-ethyl-1-methylbutyl group, a 1,2,3-trimethylbutyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neononadecyl group, a n-icosyl group, an isoicosyl group, a sec-icosyl group, a tert-icosyl group, a neoicosyl group, a n-henicosyl group, an isohenicosyl group, a sec-henicosyl group, a tert-henicosyl group, a neohenicosyl group, a n-docosyl group, an isodocosyl group, a sec-docosyl group, a tert-docosyl group, a neodocosyl group, a n-tricosyl group, an isotricosyl group, a sec-tricosyl group, a tert-tricosyl group, a neotricosyl group, a n-tetracosyl group, an isotetracosyl group, a sec-tetracosyl group, a tert-tetracosyl group, a neotetracosyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group, a cycloicosyl group, a cyclohenicosyl group, a cyclodocosyl group, a cyclotricosyl group, a cyclotetracosyl group and the like.

The haloalkyl group shown by $R^1$ to $R^3$ and $R^5$ to $R^7$ includes one, wherein a part or all of, preferably 1 to 10 atoms of, and more preferably 1 to 3 atoms of the hydrogen atoms of an alkyl group shown by the above-described $R^1$ to $R^3$ and $R^5$ to $R^7$ are substituted by a halogen atom (e.g. a fluorine atom, a chlorine atom, a bromine atom and an iodine atom), which is specifically exemplified by a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a trifluoroethyl group, a trichloromethyl group, a tribromomethyl group, a pentafluoroethyl group, a pentachloroethyl group, a pentabromoethyl group, a pentaiodoethyl group, a trifluoropropyl group, a trichloropropyl group, a heptafluoropropyl group, a heptachloropropyl group, a heptabromopropyl group, a heptaiodopropyl group, a trifluorobutyl group, a trichlorobutyl group, a nonafluorobutyl group, a nonachlorobutyl group, a nonabromobutyl group, a nonaiodobutyl group, a trifluoropentyl group, a trichloropentyl group, a perfluoropentyl group, a perchloropentyl group, a perbromopentyl group, a periodopentyl group, a trifluorohexyl group, a trichlorohexyl group, a perfluorohexyl group, a perchlorohexyl group, a perbromohexyl group, a periodohexyl group, a trifluoroheptyl group, a trichloroheptyl group, a perfluoroheptyl group, a perchloroheptyl group, a perbromoheptyl group, a periodoheptyl group, a trifluorooctyl group, a trichlorooctyl group, a perfluorooctyl group, a perchlorooctyl group, a perbromooctyl group, a periodooctyl group, a perfluorononyl group, a perchlorononyl group, a perbromononyl group, a periodononyl group, a perfluorodecyl group, a perchlorodecyl group, a perbromodecyl group, a periododecyl group, a perfluoroundecyl group, a perchloroundecyl group, a trifluorododecyl group, a pentafluorododecyl group, a perfluorododecyl group, a trichlorododecyl group, a pentachlorododecyl group, a perchlorododecyl group, a perfluorotridecyl group, a perfluorotetradecyl group, a perfluoropentadecyl group, a perfluorohexadecyl group, a perfluoroheptadecyl group, a perfluorooctadecyl group, a perfluorononadecyl group, a perfluoroicosyl group, a perfluorohenicosyl group, a perfluorodocosyl group, a perfluorotricosyl group, a perfluorotetracosyl group, a tetrafluorocyclopentyl group, a pentafluorocyclohexyl group and the like.

The aryl group shown by $R^1$ to $R^3$ and $R^5$ to $R^7$ includes one having generally 6 to 20 carbon atoms, preferably 6 to 14 carbon atoms, which is specifically exemplified by a phenyl group, a naphthyl group, a phenanthryl group, an anthryl group, a pyrenyl group and a perylenyl group. These aryl groups may have a substituent and said substituent includes, for example, lower alkyl groups having 1 to 4 carbon atoms such as a methyl group, an ethyl group, a n-propyl group, an isopropyl group, a n-butyl group, an isobutyl group, a sec-butyl group and a tert-butyl group. A specific example of the aryl group having a substituent includes, for example, a tolyl group, a 2,3-xylyl group, a 2,4-xylyl group, a mesityl group, a n-propylphenyl group, a cumenyl group, a n-butylphenyl group, an iso-butylphenyl group, a sec-butylphenyl group and a tert-butylphenyl group.

The alkoxy group shown by $R^1$ to $R^3$ and $R^5$ to $R^7$ maybe straight chained, branched or cyclic, and includes one having generally 1 to 24 carbon atoms, preferably 1 to 8 carbon atoms and more preferably 1 to 4 carbon atoms, which is specifically exemplified by a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 2-methylbutoxy group, a 1-ethylpropoxy group, a n-hexyloxy group, an isohexyloxy group, a sec-hexyloxy group, a tert-hexyloxy group, a neohexyloxy group, a 2-methylpentyloxy group, a 3-methylpentyloxy group, a 1,2-dimethylbutoxy group, a 2,2-dimethylbutoxy group, a 1-ethylbutoxy group, a 2-ethylbutoxy group, a n-heptyloxy group, an isoheptyloxy group, a sec-heptyloxy group, a tert-heptyloxy group, a neoheptyloxy group, a 2-methylhexyloxy group, a 3-methylhexyloxy group, a 2,2-dimethylpentyloxy group, 3-ethylpentyloxy group, a 2,4-dimethylpentyloxy group, a 1-ethyl-1-methylbutyloxy group, a 1,2,3-trimethylbutyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, tert-decyloxy group, a neodecyloxy group, a n-undecyloxy group, an isoundecyloxy group, a sec-undecyoxy group, a tert-undecyloxy group, a neoundecyloxy group, a n-dodecyloxy group, an isododecyloxy group, a sec-dodecyloxy group, a tert-dodecyloxy group, a neododecyloxy group, n-tridecyloxy group, an isotridecyloxy group, sec-tridecyloxy group, a tert-tridecyloxy group, a neotridecyloxy group, a n-tetradecyloxy group, an isotetradecyloxy group, a sec-tetradecyloxy group, a tert-tetradecyloxy group, a neoteradecyloxy group, a n-pentadecyloxy group, an isopentadecyloxy group, a sec-pentadecyloxy group, a tert-pentadecyloxy group, a neopentadecyloxy group, a n-hexadecyloxy group, an isohexadecyl group, a sec-hexadecyloxy group, a tert-hexadecyloxy group, a neohexadecyloxy group, a n-heptadecyloxy group, an isoheptadecyloxy group, a sec-heptadecyloxy group, a tert-heptadecyloxy group, a neoheptadecyloxy group, a n-octadecyloxy group, an isooctadecyloxy group, a sec-octadecyloxy group, a tert-octadecyloxy group, a neooctadecyloxy group, a n-nonadecyloxy group, an isononadecyloxy group, a sec-nonadecyloxy group, a tert-nonadecyloxy group, a neononadecyloxy group, a n-icosyloxy group, an isoicosyloxy group, a sec-icosyloxy group, a tert-icosyloxy group, a neoicosyloxy group, a n-henicosyloxy group, an isohenicosyloxy group, a sec-henicosyloxy group, a tert-henicosyloxy group, a neohenicosyloxy group, a n-docosyloxy group, an isodocosyloxy group, a sec-docosyloxy group, a tert-docosyloxy group, a neodocosyloxy group, a n-tricosyloxy group, an isotricosyloxy group, a sec-tricosyloxy group, a tert-tricosyloxy group, a neotricosyloxy group, a n-tetracosyloxy group, an isotetracosyloxy group, a sec-tetracosyloxy group, a tert-tetracosyloxy group, a neotetracosyloxy group, a cyclopropyloxy group, a cyclobutyloxy group, cyclopentyloxy group, a cyclohexyloxy group, a cycloheptyloxy group, a cyclooctyloxy group, a cyclononyloxy group, a cyclodecyloxy group, a cycloundecyloxy group, a cyclododecyloxy group, a cyclotridecyloxy group, a cyclotetradecyloxy group, a cyclopentadecyloxy group, a cyclohexadecyloxy group, a cycloheptadecyloxy group, a cyclooctadecyloxy group, a cyclononadecyloxy group, a cycloicosyloxy group, a cyclohenicosyloxy group, a cyclodocosyloxy group, a cyclotricosyloxy group, a cyclotetracosyloxy group and the like.

The aryloxy group shown by $R^1$ to $R^3$ and $R^5$ to $R^7$ includes one having generally 6 to 20 carbon atoms, preferably 6 to 14 carbon atoms, which is specifically exemplified by a phenoxy group, a naphthyloxy group, a phenanthryloxy group, an anthryloxy group, a pyrenyloxy group and a perylenyloxy group. These aryloxy groups may have a substituent and said substituent includes, for example, lower alkyl groups having 1 to 4 carbon atoms such as a methyl group, an ethyl group, a n-propyl group, an isopropyl group, a n-butyl group, an isobutyl group, a sec-butyl group and a tert-butyl group. A specific example of the aryloxy group having a substituent includes, for example, a tolyloxy group, a 2,3-xylyloxy group, a 2,4-xylyloxy group, a mesityloxy group, a n-propylphenoxy group, an iso-propylphenoxy group, a n-butylphenoxy group, an iso-butylphenoxy group, a sec-butylphenoxy group and a tert-butylphenoxy group.

The alkylthio group shown by $R^1$ to $R^3$ and $R^5$ to $R^7$ includes one, wherein an oxygen atom of the above-described alkoxy group is substituted by a sulfur atom.

The arylthio group shown by $R^1$ to $R^3$ and $R^5$ to $R^7$ includes one, wherein an oxygen atom of the above-described aryloxy group is substituted by a sulfur atom.

The amino group which may be substituted, shown by $R^1$ to $R^3$ and $R^5$ to $R^7$ includes one which may replace one or two hydrogen atoms of an amino group by a substituent such as a lower alkyl group or a lower alkoxy group.

The lower alkyl group as the substituent may be straight chained, branched or cyclic, and includes one having generally 1 to 6 carbon atoms, preferably 1 to 3 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 3-methylpentyl group, a 1,2-dimethylbutyl group, a 2,2-dimethylbutyl group, a 1-ethylbutyl group, a 2-ethylbutyl group, a cyclopropyl group, a cyclobutyl group, a cyclopentyl group, a cyclohexyl group and the like.

The lower alkoxy group as the substituent may be straight chained, branched or cyclic, and includes one having generally 1 to 6 carbon atoms, preferably 1 to 3 carbon atoms, which is specifically exemplified by a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, neopentyloxy group, a 2-methylbutoxy group, a 1-ethylpropoxy group, a n-hexyloxy group, an isohexyloxy group, a sec-hexyloxy group, a tert-hexyloxy group, a neohexyloxy group, a 2-methylpentyloxy group, a 3-methylpentyloxy group, a 1,2-dimethylbutoxy group, a 2,2-dimethylbutoxy group, a 1-ethylbutoxy group, a 2-ethylbutoxy group, a cyclopropyloxy group, a cyclobutyloxy group, a cyclopentyloxy group, a cyclohexyloxy group and the like.

In the general formulae [1], [2], [34], [35], [40] and [41], the lower alkylene chain shown by $Q_1$ and $Q_2$ includes a linear alkylene group having generally 1 to 6 carbon atoms, preferably 1 to 2 carbon atoms, which is specifically exemplified by a methylene group, an ethylene group, a trimethylene group, a tetramethylene group, a pentamethylene group, a hexamethylene group and the like, and among others, a methylene group, an ethylene group and the like are preferable.

The alkylene group of the alkylene group which may have a substituent, shown by $T_1$ and $T_2$ may be straight chained, branched or cyclic, and includes one having generally 1 to 24 carbon atoms, preferably 1 to 6 carbon atoms and more preferably 1 to 2 carbon atoms, which is specifically exemplified by linear alkylene group such as a methylene group, an ethylene group, a trimethylene group, a tetramethylene group, a pentamethylene group, a hexamethylene group, a heptamethylene group, an octamethylene group, a nonamethylene group, a decamethylene group, a hendecamethylene group, a dodecamethylene group, a tridecamethylene group, a tetradecamethylene group, a pentadecamethylene group, a hexadecamethylene group, a heptadecamethylene group, an octadecamethylene group, a nonadecamethylene group, an icosamethylene group, a henicosamethylene group, a docosamethylene group, tricosamethylene group and a tetracosamethylene group; branched alkylenes group such as an ethylidene group, a propylene group, an isopropylidene group, a 1-methyltrimethylene group, a 2-methyltrimethylene group, a 1,1-dimethylethylene group, a 1,2-dimethylethylne group, an ethylethylene group, a 1-methyltetramethylene group, a 1,1-dimethyltrimethylene group, a 2,2-dimethyltrimethylene group, a 2-ethyltrimethylene group, a 1-methylpentamethylene group, a 2-methylpentamethylene group, a 1,3-dimethyltetramethylene group, a 3-ethyltetramethylene group, a 1-methylhexamethylene group, a 1-methylheptamethylene group, a 1,4-diethyltetramethylene group, a 2,4-dimethylheptamethylene group, a 1-methyloctamethylene group, a 1-methylnonamethylene group, a 1-methyldecamethylene group, a 1-methylhendecamethylene group, a 1-methyldodecamethylene group, a 1-methyltridecamethylene group, a 1-methyltetradecamethylene group, a 1-methylpentadecamethylene group, a 1-methylhexadecamethylene group, a 1-methylheptadecamethylene group, a 1-methyloctadecamethylene group, a 1-methylnonadecamethylene group, a 1-methylicosamethylene group, a 1-methylhenicosamethylene group, a 1-methyldocosamethylene group and a 1-methyltricosamethylene group; and cyclic alkylene groups such as a cyclopropylene group, a 1,3-cyclobutylene group, a 1,3-cyclopentylene group, a 1,4-cyclohexylene group, a 1,5cycloheptylene group, a 1,5-cyclooctylene group, a 1,5-cyclononylene group, a 1,6-cyclodecylene group, a 1,6-cycloundecylene group, a 1,6-cyclododecylene group, a 1,7-cyclotridecylene group, a 1,7-cyclotetradecylene group, a 1,7-cyclopentadecylene group, a 1,8-cyclohexadecylene group, a 1,8-cycloheptadecylene group, a 1,8-cyclooctadecylene group, a 1,9-cyclononadecylene group, a 1,10-cycloicosylene group, a 1,10-cyclodocosylene group, a 1,11-cyclotricosylene group and a 1,11-cyclotetracosylene group.

The arylene group of the arylene group which may have a substituent, shown by $T_1$ and $T_2$ includes one having generally 6 to 15 carbon atoms, preferably 6 to 10 carbon atoms, which is specifically exemplified by an o-phenylene group, a m-phenylene group, a p-phenylene group, a 4,4'-biphenylene group, a 2,7-naphthylene group, a p-xylene-α,α'-diyl group and a m-xylene-α,α'-diyl group and the like.

The halogen atom, the alkyl group, the haloalkyl group, the aryl group, the alkoxy group, the aryloxy group, the alkylthio group, the arylthio group and the amino group which may be substituted, which are included as the substituent of an alkylene group or an arylene group, which may have a substituent, shown by $T_1$ and $T_2$ includes the same as examples of the halogen atom, the alkyl group, the haloalkyl group, the aryl group, the alkoxy group, the aryloxy group, the alkylthio group, the arylthio group and the amino group which may be substituted, shown by $R^1$ to $R^3$ and $R^5$ to $R^7$ in the above described general formulae [1], [2], [34], [35], [40] and [41].

In the above described general formulae [1], [35] and [40], the alkyl group of the alkyl group which may have a substituent, shown by $R^4$, $R^{4'''}$ and $R^{4''''}$ includes the same as examples of the alkyl group shown by $R^1$ to $R^3$ and $R^5$ to $R^7$ in the above-described general formulae [1], [2], [34], [35], [40] and [41].

The alkenyl group of the alkenyl group which may have a substituent, shown by $R^4$, $R^{4'''}$ and $R^{4''''}$ may be straight chained, branched or cyclic, and includes one having generally 2 to 24 carbon atoms, preferably 2 to 8 carbon atoms and more preferably 2 to 4 carbon atoms, which is specifically exemplified by a vinyl group, a 1-propenyl group, an allyl group, an isopropenyl group, a 1-butenyl group, a 2-butenyl group, a 3-butenyl group, a 1-methyl-2-propenyl group, a 1,3-butadienyl group, a 1-pentenyl group, a 2-pentenyl group, a 3-pentenyl group, a 4-pentenyl group, a 1,3-pentadienyl group, a 2,4-pentadienyl group, a 1,1-dimethyl-2-propenyl group, a 1-ethyl-2-propenyl group, a 1,2-dimethyl-1-propenyl group, a 1-methyl-1-butenyl group, a 1-methyl-2-butenyl group, a 1-hexenyl group, a 2-hexenyl group, a 3-hexenyl group, a 4-hexenyl group, a 5-hexenyl group, a 1-methyl-1-pentenyl group, a 2-methyl-2-pentenyl group, a 3-methyl-1,3-pentadienyl group, a 1-heptenyl group, a 2-heptenyl group, a 3-heptenyl group, a 4-heptenyl group, a 5-heptenyl group, a 6-heptenyl group, a 1-octenyl group, a 2-octenyl group, a 3-octenyl group, a 4-octenyl group, a 5-octenyl group, a 6-octenyl group, a 7-octenyl group, a 1-nonenyl group, a 2-nonenyl group, a 3-nonenyl group, a 4-nonenyl group, a 5-nonenyl group, a 6-nonenyl group, a 7-nonenyl group, a 8-nonenyl group, a 1-decenyl group, a 2-decenyl group, a 3-decenyl group, a 4-decenyl group, a 5-decenyl group, a 6-decenyl group, a 7-decenyl group, a 8-decenyl group, a 9-decenyl group, a 1-undecenyl group, a 2-undecenyl group, a 3-undecenyl group, a 4-undecenyl group, a 5-undecenyl group, a 6-undecenyl group, a 7-undecenyl group, a 8-undecenyl group, a 9-undecenyl group, a 10-undecenyl group, a 1-dodecenyl group, a 2-dodecenyl group, a 10-dodecenyl group, a 11-dodecenyl group, a 1-tridecenyl group, a 2-tridecenyl group, a 3-tridecenyl group, a 11-tridecenyl group, a 12-tridecenyl group, a 1-tetradecenyl group, a 2-tetradecenyl group, a 13-tetradecenyl group, a 1-pentadecenyl group, a 5-pentadecenyl group, a 13-pentadecenyl group, a 1-hexadecenyl group, a 2-hexadecenyl group, a 15-hexadecenyl group, a 1-heptadecenyl group, a 2-heptadecenyl group, a 15-heptadecenyl group, a 16-heptadecenyl group, a 1-octadecenyl group, a 2-octadecenyl group, a 16-octadecenyl group, a 17-octadecenyl group, a 1-nonadecenyl group, a 2-nonadecenyl group, a 16-nonadecenyl group, a 1-icosenyl group, a 2-icosenyl group, a 18-icosenyl group, a 1-henicosenyl group, a 2-henicosenyl group, a 19-henicosenyl group, a 1-docosenyl group, a 2-docosenyl group, a 20-docosenyl group, a 1-tricosenyl group, a 2-tricosenyl group, a 20-tricosenyl group, a 1-tetracosenyl group, a 2-tetracosenyl group, a 8-tetracosenyl group, a 20-tetracosenyl group, a 2-cyclopropenyl group, a 2-cyclopentenyl group, a 2,4-cyclopentadienyl group, a 2-cyclohexenyl group, a 3-cyclohexenyl group, a 2-cycloheptenyl group, a 2-cyclononenyl group, a 3-cyclodocecenyl group, a 2-cycloundecenyl group, a 2-cyclododecenyl group, a 2-cyclotridecenyl group, a 2-cyclotetradecenyl group, a 2-cyclopentadecenyl group, a 2-cyclohexadecenyl group, a 2-cycloheptadecenyl group, a 2-cyclooctadecenyl group, a 2-cyclononadecenyl group, a 2-cycloicosenyl group, a 2-cyclohenicosenyl group, a 2-cyclodocosenyl group, a 2-cyclotricosenyl group, a 2-cyclotetracosenyl group and the like.

The aryl group of the aryl group which may have a substituent, shown by $R^4$, $R^{4'''}$ and $R^{4''''}$ includes one having generally 6 to 20 carbon atoms, preferably 6 to 14 carbon atoms, which is specifically exemplified by a phenyl group, a naphthyl group, an anthryl group, a phenanthryl group, a pyrenyl group, a perylenyl group and the like.

The aralkyl group of the aralkyl group which may have a substituent, shown by $R^4$, $R^{4'''}$ and $R^{4''''}$ includes one, wherein a hydrogen atom of the alkyl group of the alkyl group which may have a substituent, shown by the above-described $R^4$, $R^{4'''}$ and $R^{4''''}$, is substituted by an aryl group which may have a substituent, shown by the above-described $R^4$, $R^{4'''}$ and $R^{4''''}$ and includes one having generally 7 to 21 carbon atoms, preferably 7 to 15 carbon atoms, which is specifically exemplified by a benzyl group, a phenethyl group, a phenylpropyl group, a phenylbutyl group, a phenylpentyl group, a phenylhexyl group, a phenylcyclohexyl group, a phenylheptyl group, a phenyl-1-methylhexyl group, a phenyloctyl group, a phenylnonyl group, a phenyldecyl group, a phenylundecyl group, a phenyldodecyl group, a phenyltridecyl group, a phenyltetradecyl group, a phenylpentadecyl group and the like.

The halogen atom, the alkyl group, the haloalkyl group, the aryl group, the alkoxy group, the aryloxy group, the alkylthio group, the arylthio group and the amino group which may be substituted, included as the substituent of an alkyl group, an alkenyl group, an aryl group and an aralkyl group, which may have a substituent, shown by $R^4$, $R^{4'''}$ and $R^{4''''}$ includes the same as examples of the halogen atom, the alkyl group, the haloalkyl group, the aryl group, the alkoxy group, the aryloxy group, the alkylthio group, the arylthio group and the amino group which may be substituted, shown by $R^1$ to $R^3$ and $R^5$ to $R^7$ in the above-described general formulae [1], [2], [34], [35], [40] and [41].

In the general formulae [1], [2], [34], [35], [40] and [41], m is an integer of generally 0 to 4, preferably 0 to 2 and more preferably 0.

n is an integer of generally 0 to 5, preferably 0 to 3 and more preferably 0.

In the general formulae [1] and [2], the counter anion shown by $A_1$ to $A_3$ includes, for example, one derived from a compound shown by the general formula [7]:

$$HM^1(R^{11})_4 \qquad [7]$$

(wherein $M^1$ is a boron atom or a gallium atom; $R^{11}$ is an aryl group which may have a substituent selected from the group consisting of a lower haloalkyl group, a halogen atom, a nitro group and a cyano group), an organic acid or an inorganic acid, or a halogen atom.

The organic acid includes, for example, a carboxylic acid shown by the general formula [8]:

$$R^{12}{-}COOH \qquad [8]$$

(wherein $R^{12}$ is a hydrogen atom, or an alkyl group, an alkenyl group, an aryl group or an aralkyl group, which may have a halogen atom), or a sulfonic acid shown by the general formula [9]:

$$R^{13}{-}SO_3H \qquad [9]$$

(wherein $R^{13}$ is an alkyl group, an aryl group or an aralkyl group, which may have a halogen atom) and the like.

The inorganic acid includes, for example, nitric acid, sulfuric acid, halosulfuric acid, perhalogenic acid, or a compound shown by the general formula [10]:

$$HM^2F_1 \qquad [10]$$

(wherein $M^2$ is a metalloid atom or a metal atom; and 1 is an integer of 4 or 6).

In the general formulae [40] and [41], the anion derived from the organic acid shown by $A_1''$ to $A_3''$ includes one derived from a carboxylic acid shown by the above-described general formula [8] and a sulfonic acid shown by the general formula [9].

The anion derived from the inorganic acid shown by $A_1''$ to $A_3''$ includes one derived from nitric acid, sulfuric acid, halosulfuric acid, perhalogenic acid and a compound shown by the above-described general formula [10].

In the general formula [7], the aryl group of the aryl group which may have a substituent selected from the group consisting of a lower alkyl group, a halogen atom, a nitro group and a cyano group, shown by $R^{11}$ includes one having generally 6 to 20, preferably 6 to 10 carbon atoms, which is specifically exemplified by a phenyl group, a naphthyl group, an anthryl group, a phenanthryl group, a pyrenyl group, a perylenyl group and the like, and among others, a phenyl group is preferable.

The lower haloalkyl group as the substituent may be straight chained, branched or cyclic, and includes one having generally 1 to 4 carbon atoms, preferably 1 to 2 carbon atoms, which is specifically exemplified by a fluoromethyl group, a difluoromethyl group, a trifluoromethyl group, a chloromethyl group, a dichloromethyl group, a trichloromethyl group, a tribromomethyl group, a triiodomethyl group, a pentafluoroethyl group, a pentachloroethyl group, a pentabromoethyl group, a pentaiodoethyl group, a heptafluoropropyl group, a heptachloropropyl group, a heptabromopropyl group, a heptaiodopropyl group, a nonafluorobutyl group, a nonachlorobutyl group, a nonabromobutyl group, a nonaiodobutyl group and the like.

The halogen atom as the substituent includes, for example, a fluorine atom, a chlorine atom, a bromine atom, an iodine atom and the like.

The halogen atom as the counter anion shown by $A_1$ to $A_3$ includes, for example, a fluorine atom, a chlorine atom, a bromine atom, an iodine atom and the like.

In the general formula [8], the alkyl group of the alkyl group which may have a halogen atom, shown by $R^{12}$ may be straight chained, branched or cyclic, and includes one having generally 1 to 23 carbon atoms, preferably 1 to 11 carbon atoms, which is specifically exemplified by the same as all examples of one having 1 to 23 carbon atoms, among the alkyl groups shown by $R^1$ to $R^3$ and $R^5$ to $R^7$ in the above-described general formulae [1], [2], [34], [35], [40] and [41], and among others, for example, a methyl group, a propyl group, a heptyl group and an undecyl group are preferable.

The alkenyl group of the alkenyl group which may have a halogen atom, shown by $R^{12}$ may be-straight chained, branched or cyclic, and includes one having generally 2 to 23 carbon atoms, preferably 2 to 11 carbon atoms, which is specifically exemplified by the same as all examples of one having 2 to 23 carbon atoms, among the alkenyl groups of the alkenyl group which may have a substituent, shown by $R^4$, $R^{4'''}$ and $R^{4''''}$ in the above-described general formulae [1], [35] and [40].

The aryl group of the aryl group which may have a halogen atom, shown by $R^{12}$ includes one having generally 6 to 20 carbon atoms, preferably 6 to 14 carbon atoms, which is specifically exemplified by a phenyl group, a naphthyl group, an anthryl group, a phenanthryl group, a pyrenyl group and the like, and among others, a phenyl group is preferable.

The aralkyl group of the aralkyl group which may have a halogen atom, shown by $R^{12}$ includes one, wherein a hydrogen atom of the above-described alkyl group is substituted by the above-described aryl group and includes one having generally 7 to 13 carbon atoms, preferably 7 to 10 carbon atoms, which is specifically exemplified by a benzyl group, a phenethyl group, a phenylpropyl group, a phenylbutyl group, a phenylpentyl group, a phenylhexyl group, a phenylheptyl group, a phenyl-1-methylhexyl group and the like, and among others, a benzyl group and a phenethyl group are preferable.

The halogen atom of the alkyl group, the alkenyl group, the aryl group or the aralkyl group, which may have a halogen atom, shown by $R^{12}$ includes, for example, a fluorine atom, a chlorine atom, a bromine atom, an iodine atom and the like.

The alkyl group, the alkenyl group, the aryl group or the aralkyl group, which may have a halogen atom, shown by $R^{12}$ includes one, wherein a part or all of hydrogen atoms of the above-described alkyl group, alkenyl group, aryl group or aralkyl group are substituted by a halogen atom.

Specifically, in the alkyl group, it is preferable that 1 to 47 of, preferably 23 to 47 of, more preferably all of hydrogen atoms thereof are substituted by halogen atoms.

In the alkenyl group, it is preferable that 1 to 45 of, preferably 21 to 45 of, more preferably all of hydrogen atoms thereof are substituted by halogen atoms.

In the aryl group, it is preferable that 1 to 5 of, preferably all of hydrogen atoms in the ring thereof are substituted by halogen atoms.

The aralkyl group includes one, wherein a hydrogen atom of alkyl group part and/or a hydrogen atom of aryl group part thereof is substituted by a halogen atom, and in the alkyl group part, preferably a part of hydrogen atoms thereof are substituted, and in the aryl group part, 1 to 5 of, preferably all of hydrogen atoms in the ring thereof are substituted.

In the general formula [9], the alkyl group of an alkyl group which may have a halogen atom, shown by $R^{13}$ may be straight chained, branched or cyclic, and includes one having generally 1 to 24 carbon atoms, preferably 1 to 8 carbon atoms, which is specifically exemplified by, for example, the same as examples of the alkyl group shown by $R^1$ to $R^3$ and $R^5$ to $R^7$ in the above-described general formulae [1], [2], [34], [35], [40] and [41] and bicyclo[2.2.1]heptane, and among others, a methyl group, a butyl group, an octyl group and the like are preferable.

The aryl group of the aryl group which may have a halogen atom, shown by $R^{13}$ includes one having generally 6 to 20 carbon atoms, preferably 6 to 14 carbon atoms, which is specifically exemplified by a phenyl group, a naphthyl group, an anthryl group, a phenanthryl group, a pyrenyl group, a perylenyl group and the like, and among others, a phenyl group is preferable.

The aralkyl group of the aralkyl group which may have a halogen atom, shown by $R^{13}$ includes one having generally 7 to 15 carbon atoms, preferably 7 to 10 carbon atoms, which is specifically exemplified by a benzyl group, a phenethyl group, a phenylpropyl group, a phenylbutyl group, a phenylpentyl group, a phenylhexyl group, a phenylheptyl group, a phenyloctyl group, a phenylnonyl group and the like, and among others, a benzyl group and a phenethyl group are preferable.

The halogen atom of the alkyl group, the aryl group or the aralkyl group, which may have a halogen atom, shown by $R^{13}$ includes, for example, a fluorine atom, a chlorine atom, a bromine atom and an iodine atom.

The alkyl group, the aryl group or the aralkyl group, which may have a halogen atom, shown by $R^{13}$ includes one, wherein a part or all of hydrogen atoms of the above-described alkyl group, aryl group or aralkyl group are substituted by halogen atoms.

Specifically, in the alkyl group, it is preferable that 1 to 49 of, preferably 17 to 49 of, more preferably all of hydrogen atoms thereof are substituted by halogen atoms.

In the aryl group, it is preferable that 1 to 5 of, preferably all of hydrogen atoms in the ring thereof are substituted by halogen atoms.

The aralkyl group includes one, wherein a hydrogen atom of alkyl group part and/or a hydrogen atom of aryl group part thereof is substituted by a halogen atom, and in the alkyl group part, preferably a part of hydrogen atoms thereof are substituted, and in the aryl group part, 1 to 5 of, preferably all of hydrogen atoms in the ring thereof are substituted.

The alkyl group, the alkenyl group, the aryl group or the aralkyl group, which may have a halogen atom, shown by $R^{12}$ in the general formula [8] and the alkyl group, the alkenyl group, the aryl group or the aralkyl group, which may have a halogen atom, shown by $R^{13}$ in the general formula [9] may further have other substituent, and said substituent includes, for example, lower alkyl groups having 1 to 4 carbon atoms such as a methyl group, an ethyl group, a n-propyl group, an isopropyl group, a n-butyl group, an isobutyl group, a sec-butyl group and a tert-butyl group; lower haloalkyl groups having 1 to 4 carbon atoms such as a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a trifluoroethyl group, a trichloromethyl group, a tribromomethyl group, a pentafluoroethyl group, a pentachloroethyl group, a heptafluoropropyl group and a nonafluorobutyl group; lower alkoxy groups having 1 to 4 carbon atoms such as a methoxy group, an ethoxy group, a n-propoxy group, an isopropoxy group, a n-butoxy group, an isobutoxy group, a sec-butoxy group and a tert-butoxy group; an amino group, a nitro group, an oxo group, a carbonyl group, a hydroxyl group and an aldehyde group.

In the general formula [10], the metalloid atom shown by $M^2$ includes a boron atom, a silicon atom, a phosphorous atom, an arsenium atom and an antimony atom, and among others, a phosphorous atom, a arsenic atom, an antimony atom and the like are preferable.

The metal atom shown by $M^2$ includes an aluminum atom, a titanium atom, an iron atom, a nickel atom, a gallium atom, a zirconium atom and the like.

The specific examples of the compound shown by the general formula [7] are, for example, tetraphenyl borate, tetrakis[4-(trifluoromethyl)phenyl]borate, tetrakis[4-(trichloromethyl)phenyl]borate, tetrakis[4-(tribromomethyl)phenyl]borate, tetrakis[4-(triiodomethyl)phenyl]borate, tetrakis[3,5-bis (trifluoromethyl)phenyl]borate, tetrakis[3,5-bis (trichloromethyl)phenyl]borate, tetrakis[3,5-bis (tribromomethyl)phenyl]borate, tetrakis[3,5-bis (triiodomethyl)phenyl]borate, tetrakis(pentafluorophenyl) borate, tetrakis(pentachlorophenyl) borate, tetrakis(pentabromophenyl) borate, tetrakis(pentaiodophenyl) borate, tetraphenyl gallate, tetrakis[4-(trifluoromethyl) phenyl]gallate, tetrakis[4-(trichloromethyl) phenyl]gallate, tetrakis[4-(tribromomethyl) phenyl]gallate, tetrakis[4-(triiodomethyl) phenyl]gallate, tetrakis[3,5-bis (trifluoromethyl)phenyl]gallate, tetrakis[3,5-bis (trichloromethyl)phenyl]gallate, tetrakis[3,5-bis (tribromomethyl)phenyl]gallate, tetrakis[3,5-bis (triiodomethyl)phenyl]gallate, tetrakis(pentafluorophenyl)gallate, tetrakis(pentachlorophenyl)gallate, tetrakis(pentabromophenyl)gallate and tetrakis(pentaiodophenyl)gallate, and among others, tetraphenyl borate, tetrakis[4-(trifluoromethyl)phenyl]borate, tetrakis[3,5-bis(trifluoromethyl)phenyl]borate, tetrakis(pentafluorophenyl) borate, tetraphenyl gallate, tetrakis[4-(trifluoromethyl)phenyl]gallate, tetrakis[3,5-bis(trifluoromethyl)phenyl]gallate and tetrakis(pentafluorophenyl) gallate are preferable.

The specific examples of the carboxylic acid shown by the general formula [8] are aliphatic saturated carboxylic acids such as formic acid, acetic acid, propionic acid, butyric acid, isobutyric acid, valeric acid, isovaleric acid, pivalic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, icosanoic acid, henicosanoic acid, docosanoic acid and tricosanoic acid; alicyclic carboxylic acids such as cyclohexylcarboxylic acid; halogenated alkylcarboxylic acids such as fluoroacetic acid, difluoroacetic acid, trifluoroacetic acid, chloroacetic acid, dichloroacetic acid, trichloroacetic acid, bromoacetic acid, dibromoacetic acid, tribromoacetic acid, iodoacetic acid, diiodoacetic acid, triiodoacetic acid, trifluoropropionic acid, perfluoropropionic acid, trichloropropionic acid, perchloropropionic acid, perbromopropionic acid, periodopropionic acid, trifluorobutyric acid, perfluorobutyric acid, trichlorobutyric acid, perchlorobutyric acid, perbromobutyric acid, periodobutyric acid, trifluorovaleric acid, perfluorovaleric acid, perchlorovaleric acid, perbromovaleric acid, periodovaleric acid, trifluorohexanoic acid, trichlorohexanoic acid, perfluorohexanoic acid, perchlorohexanoic acid, perbromohexanoic acid, periodohexanoic acid, trifluoroheptanoic acid, trichloroheptanoic acid, perfluoroheptanoic acid, perchloroheptanoic acid, perbromoheptanoic acid, periodoheptanoic acid, trifluorooctanoic acid, trichlorooctanoic acid, perfluorooctanoic acid, perchlorooctanoic acid, perbromooctanoic acid, periodooctanoic acid, trifluorononanoic acid, trichlorononanoic acid, perfluorononanoic acid, perchlorononanoic acid, perbromononanoic acid, periodononanoic acid, trifluorodecanoic acid, trichlorodecanoic acid, perfluorodecanoic acid, perchlorodecanoic acid, perbromodecanoic acid, periododecanoic acid, trifluoroundecanoic acid, trichloroundecanoic acid, perfluoroundecanoic acid, perchloroundecanoic acid, perbromoundecanoic acid, periodoundecanoic acid, trifluorododecanoic acid, trichlorododecanoic acid, perfluorododecanoic acid, perchlorododecanoic acid, perbromododecanoic acid, periodododecanoic acid, trifluorotridecanoic acid, trichlorotridecanoic acid, perfluorotridecanoic acid, perchlorotridecanoic acid, perbromotridecanoic acid, periodotridecanoic acid, trifluorotetradecanoic acid, trichlorotetradecanoic acid, perfluorotetradecanoic acid, perchlorotetradecanoic acid, perbromotetradecanoic acid, periodotetradecanoic acid, trifluoropentadecanoic acid, trichloropentadecanoic acid, perfluoropentadecanoic acid, perchloropentadecanoic acid, perbromopentadecanoic acid, periodopentadecanoic acid, perfluorohexadecanoic acid, perchlorohexadecanoic acid, perbromohexadecanoic acid, periodohexadecanoic acid, perfluoroheptadecanoic acid, perchloroheptadecanoic acid, perbromoheptadecanoic acid, periodoheptadecanoic acid, perfluorooctadecanoic acid, perchlorooctadecanoic acid, perbromooctadecanoic acid, periodooctadecanoic acid, perfluorononadecanoic acid, perchlorononadecanoic acid, perbromononadecanoic acid, periodononadecanoic acid, perfluoroicosanoic acid, perchloroicosanoic acid, perbromoicosanoic acid, periodoicosanoic acid, perfluorohenicosanoic acid, perchlorohenicosanoic acid, perbromohenicosanoic acid, periodohenicosanoic acid, perfluorodocosanoic acid, perchlorodocosanoic acid, perbromodocosanoic acid, periododocosanoic acid, perfluorotricosanoic acid, perchlorotricosanoic acid, perbromotricosanoic acid and periodotricosanoic acid; hydroxylated aliphatic carboxylic acids such as glycolic acid, lactic acid, glyceric acid and 3-hydroxy-2-methylpropionic acid; aliphatic ketonic carboxylic acids such as pyruvic acid, acetoacetic acid, 5-oxovaleric acid; aliphatic unsaturated carboxylic acids such as acrylic acid, methacrylic acid, crotonic acid, isocrotonic acid, 2-pentenoic acid, 3-hexenoic acid, 3-heptenoic acid, 4-octenoic acid, 4-nonenoic acid, 5-decenoic acid, 5-undecenoic acid, 6-dodecenoic acid, 6-tridecenoic acid, 7-tetradecenoic acid, 7-pentadecenoic acid, 8-hexadecenoic acid, 8-heptadecenoic acid, oleic acid, elaidic acid, 9-nonadecenoic acid, 10-icosenoic acid, 10-henicosenoic acid, 11-docosenoic acid and 11-tricosenoic acid; alicyclic carboxylic acids such as camphor carboxylic acid and adamantane carboxylic acid; aromatic carboxylic acids such as benzoic acid, naphthoic acid, anthracene carboxylic acid, pyrene carboxylic acid, perylene carboxylic acid and pentaphene carboxylic acid; alkylaromatic carboxylic acids such as toluic acid; halogenated aromatic carboxylic acids such as fluorobenzoic acid, chlorobenzoic acid, bromobenzoic acid, iodobenzoic acid, difluorobenzoic acid, dichlorobenzoic acid, dibromobenzoic acid, diiodobenzoic acid, trifluorobenzoic acid, trichlorobenzoic acid, tribromobenzoic acid, triiodobenzoic acid, tetrafluorobenzoic acid, tetrachlorobenzoic acid, tetrabromobenzoic acid, tetraiodobenzoic acid, pentafluorobenzoic acid, pentachlorobenzoic acid, pentabromobenzoic acid, pentaiodobenzoic acid, fluoronaphthoic acid, chloronaphthoic acid, bromonaphthoic acid, iodonaphthoic acid, perfluoronaphthoic acid, perchloronaphthoic acid, perbromonaphthoic acid and periodonaphthoic acid; halogenated alkylaromatic carboxylic acids such as trifluoromethylbenzoic acid, trichloromethylbenzoic acid, tribromomethylbenzoic acid, triiodomethylbenzoic acid, bis(trifluoromethyl)benzoic acid, bis(trichloromethyl)benzoic acid, bis(tribromomethyl)benzoic acid, bis(triiodomethyl)benzoic acid, tris(trifluoromethyl)benzoic acid, tris(trichloromethyl)benzoic acid, tris(tribromomethyl)benzoic acid, tris(triiodomethyl)benzoic acid, trifluoromethylnaphthoic acid, trichloromethylnaphthoic acid, tribromomethylnaphthoic acid, triiodomethylnaphthoic acid, bis(trifluoromethyl)naphthoic acid, bis(trichloromethyl)naphthoic acid, bis(tribromomethyl)naphthoic acid, bis(triiodomethyl)naphthoic acid, tris(trifluoromethyl)naphthoic acid, tris(trichloromethyl)naphthoic acid, tris(tribromomethyl)naphthoic acid and tris(triiodomethyl)naphthoic acid; alkoxyaromatic carboxylic acids such as anisic acid, veratric acid, o-veratric acid and gallic acid; halogenated alkoxyaromatic carboxylic acids such as trifluoromethoxybenzoic acid, pentafluoroethoxybenzoic acid, trichloromethoxybenzoic acid, pentachloroethoxybenzoic acid, tribromomethoxybenzoic acid, pentabromoethoxybenzoic acid, triiodomethoxybenzoic acid and pentaiodoethoxybenzoic acid; nitro aromatic carboxylic acids such as trinitrobenzoic acid; hydroxyaromatic carboxylic acids such as salicylic acid, o-pyrocatechuic acid, β-resorcylic acid, gentisic acid, γ-resorcylic acid, protocatechuic acid and α-resorcylic acid; hydroxylated alkoxyaromatic carboxylic acids such as vanillic acid and isovanillic acid; aralkyl acids such as α-toluic acid, hydrocinnamic acid, hydroatropic acid, 3-phenylpropanoic acid, 4-phenylbutanoic acid, 5-phenylpentanoic acid, 6-phenylhexanoic acid and 7-phenylheptanoic acid; hydroxyaralkyl acids such as homogentisic acid; arylalkenyl acids such as cinnamic acid and atropic acid; hydroxyarylalkenyl acids such as umbellic acid and caffeic acid; hydroxylated alkoxyarylalkenyl acids such as ferulic acid and isoferulic acid; aromatic hydroxylalkyl carboxylic acids such as mandelic acid, benzilic acid, atrolactic acid, tropic acid and atroglyceric acid; aliphatic ketonic carboxylic acids such as pyruvic acid and acetoacetic acid; aminoaromatic acids such as anthranilic acid; amino acids such as alanine, arginine, asparagine, cysteine, glutamine, glycine, histidine, isoleucine, leucine, lysine, methionine, phenylalanine, proline, serine, threonine, tryptophane, tyrosine and valine; p-formylphenylacetic acid, 6-(2-naphthyl)hexanoic acid and the like.

The specific examples of the sulfonic acid shown by the general formula [9] are alkyl sulfonic acids such as methanesulfonic acid, ethanesulfonic acid, propanesulfonic acid, butanesulfonic acid, pentanesulfonic acid, hexanesulfonic acid, heptanesulfonic acid, octanesulfonic acid, nonanesulfonic acid, decanesulfonic acid, undecanesulfonic acid, dodecanesulfonic acid, tridecanesulfonic acid, tetradecanesulfonic acid, pentadecanesulfonic acid, hexadecanesulfonic acid, heptadecanesulfonic acid, octadecanesulfonic acid, nonadecanesulfonic acid, icosanesulfonic acid, henicosanesulfonic acid, docosanesulfonic acid, tricosanesulfonic acid and tetracosanesulfonic acid; cyclic alkyl sulfonic acids such as cyclohexane sulfonic acid and cyclopentanesulfonic acid; halogenated alkyl sulfonic acids such as fluoromethane sulfonic acid, difluoromethane sulfonic acid, trifluoromethanesulfonic acid, chloromethane sulfonic acid, dichloromethane sulfonic acid, trichloromethane sulfonic acid, bromomethane sulfonic acid, dibromomethane sulfonic acid, tribromomethane sulfonic acid, iodomethane sulfonic acid, diiodomethane sulfonic acid, triiodomethane sulfonic acid, fluoroethane sulfonic acid, difluoroethane sulfonic acid, trifluoroethane sulfonic acid, pentafluoroethane sulfonic acid, chloroethane sulfonic acid, dichloroethane sulfonic acid, trichloroethane sulfonic acid, pentachloroethane sulfonic acid, tribromoethane sulfonic acid, pentabromoethane sulfonic acid, triiodoethane sulfonic acid, pentaiodoethane sulfonic acid, fluoropropane sulfonic acid, trifluoropropane sulfonic acid, heptafluoropropane sulfonic acid, chloropropane sulfonic acid, trichloropropane sulfonic acid, heptachloropropane sulfonic acid, bromopropane sulfonic acid, tribromopropane sulfonic acid, heptabromopropane sulfonic acid, triiodopropane sulfonic acid, heptaiodopropane sulfonic acid, trifluorobutane sulfonic acid, nonafluorobutane sulfonic acid, trichlorobutane sulfonic acid, nonachlorobutane sulfonic acid, tribromobutane sulfonic acid, nonabromobutane sulfonic acid, triiodobutane sulfonic acid, nonaiodobutane sulfonic acid, trifluoropentane sulfonic acid, perfluoropentane sulfonic acid, trichloropentane sulfonic acid, perchloropentane sulfonic acid, tribromopentane sulfonic acid, perbromopentane sulfonic acid, triiodopentane sulfonic acid, periodopentane sulfonic acid, trifluorohexane sulfonic acid, perfluorohexane sulfonic acid, trichlorohexane sulfonic acid, perchlorohexane sulfonic acid, perbromohexane sulfonic acid, periodohexane sulfonic acid, trifluoroheptane sulfonic acid, perfluoroheptane sulfonic acid, trichloroheptane sulfonic acid, perchloroheptane sulfonic acid, perbromoheptane sulfonic acid, periodoheptane sulfonic acid, trifluorooctane sulfonic acid, perfluorooctane sulfonic acid, trichlorooctane sulfonic acid, perchlorooctane sulfonic acid, perbromooctane sulfonic acid, periodooctane sulfonic acid, trifluorononane sulfonic acid, perfluorononane sulfonic acid, trichlorononane sulfonic acid, perchlorononane sulfonic acid, perbromononane sulfonic acid, periodononane sulfonic acid, trifluorodecane sulfonic acid, perfluorodecane sulfonic acid, trichlorodecane sulfonic acid, perchlorodecane sulfonic acid, perbromodecane sulfonic acid, periododecane sulfonic acid, trifluoroundecane sulfonic acid, perfluoroundecane sulfonic acid, trichloroundecane sulfonic acid, perchloroundecane sulfonic acid, perbromoundecane sulfonic acid, periodoundecane sulfonic acid, trifluorododecane sulfonic acid, perfluorododecane sulfonic acid, trichlorododecane sulfonic acid, perchlorododecane sulfonic acid, perbromododecane sulfonic acid, periodododecane sulfonic acid, trifluorotridecane sulfonic acid, perfluorotridecane sulfonic acid, trichlorotridecane sulfonic acid, perchlorotridecane sulfonic acid, perbromotridecane sulfonic acid, periodotridecane sulfonic acid, trifluorotetradecane sulfonic acid, perfluorotetradecane sulfonic acid, trichlorotetradecane sulfonic acid, perchlorotetradecane sulfonic acid, perbromotetradecane sulfonic acid, periodotetradecane sulfonic acid, trifluoropentadecane sulfonic acid, perfluoropentadecane sulfonic acid, trichloropentadecane sulfonic acid, perchloropentadecane sulfonic acid, perbromopentadecane sulfonic acid, periodopentadecane sulfonic acid, perfluorohexadecane sulfonic acid, perchlorohexadecane sulfonic acid, perbromohexadecane sulfonic acid, periodohexadecane sulfonic acid, perfluoroheptadecane sulfonic acid, perchloroheptadecane sulfonic acid, perbromoheptadecane sulfonic acid, periodoheptadecane sulfonic acid, perfluorooctadecane sulfonic acid, perchlorooctadecane sulfonic acid, perbromooctadecane sulfonic acid, periodooctadecane sulfonic acid, perfluorononadecane sulfonic acid, perchlorononadecane sulfonic acid, perbromononadecane sulfonic acid, periodononadecane sulfonic acid, perfluoroicosane sulfonic acid, perchloroicosane sulfonic acid, perbromoicosane sulfonic acid, periodoicosane sulfonic acid, perfluorohenicosane sulfonic acid, perchlorohenicosane sulfonic acid, perbromohenicosane sulfonic acid, periodohenicosane sulfonic acid, perfluorodocosane sulfonic acid, perchlorodocosane sulfonic acid, perbromodocosane sulfonic acid, periododocosane sulfonic acid, perfluorotricosane sulfonic acid, perchlorotricosane sulfonic acid, perbromotricosane sulfonic acid, periodotricosane sulfonic acid, perfluorotetracosane sulfonic acid, perchlorotetracosane sulfonic acid, perbromotetracosane sulfonic acid and periodotetracosane sulfonic acid; halogenated cycloalkyl sulfonic acids such as 4-fluorocyclohexane sulfonic acid, 4-chlorocyclohexane sulfonic acid, 4-bromocyclohexane sulfonic acid, 4-iodocyclohexane sulfonic acid, 2,4-difluorocyclohexane sulfonic acid, 2,4-dichlorocyclohexane sulfonic acid, 2,4-dibromocyclohexane sulfonic acid, 2,4-diiodocyclohexane sulfonic acid, 2,4,6-trifluorocyclohexane sulfonic acid, 2,4,6-trichlorocyclohexane sulfonic acid, 2,4,6-tribromocyclohexane sulfonic acid, 2,4,6-triiodocyclohexane sulfonic acid, perfluorocyclohexane sulfonic acid, perchlorocyclohexane sulfonic acid, perbromocyclohexane sulfonic acid and periodocyclohexane sulfonic acid; aromatic sulfonic acids such as benzene sulfonic acid, naphthalene sulfonic acid, anthracene sulfonic acid, phenanthrene sulfonic acid and pyrene sulfonic acid; alkylaromatic sulfonic acids such as p-toluene sulfonic acid; halogenated aromatic sulfonic acids such as 2-fluorobenzene sulfonic acid, 3-fluorobenzene sulfonic acid, 4-fluorobenzene sulfonic acid, 2-chlorobenzene sulfonic acid, 3-chlorobenzene sulfonic acid, 4-chlorobenzene sulfonic acid, 2-bromobenzene sulfonic acid, 3-bromobenzene sulfonic acid, 4-bromobenzene sulfonic acid, 2-iodobenzene sulfonic acid, 4-iodobenzene sulfonic acid, 2,4-difluorobenzene sulfonic acid, 2,6-difluorobenzene sulfonic acid, 2,4-dichlorobenzene sulfonic acid, 2,6-dichlorobenzene sulfonic acid, 2,4-dibromobenzene sulfonic acid, 2,6-dibromobenzene sulfonic acid, 2,4-diiodobenzene sulfonic acid, 2,6-diiodobenzene sulfonic acid, 2,4,6-trifluorobenzene sulfonic acid, 3,4,5-trifluorobenzene sulfonic acid, 2,4,6-trichlorobenzene sulfonic acid, 3,4,5-trichlorobenzene sulfonic acid, 2,4,6-tribromobenzene sulfonic acid 3,4,5-tribrombenzene sulfonic acid, 2,4,6-triiodobenzene sulfonic acid, 3,4,5-triiodobenzene sulfonic acid, pentafluorobenzene sulfonic acid, pentachlorobenzene sulfonic acid, pentabromobenzene sulfonic acid and pentaiodobenzene sulfonic acid; halogenated alkylaromatic sulfonic acids such as 2-trifluoromethylbenzene sulfonic acid, 3-trifluoromethylbenzene sulfonic acid, 4-trifluoromethylbenzene sulfonic acid, 2,6-bis(trifluoromethyl)benzene sulfonic acid, 3,5-bis(trifluoromethyl)benzene sulfonic acid, 4-trichloromethylbenzene sulfonic acid, 4-tribromomethylbenzene sulfonic acid and 4-triiodomethylbenzene sulfonic acid; aralkyl sulfonic acids such as benzyl sulfonic acid, phenethyl sulfonic acid, phenylpropyl sulfonic acid, phenylbutyl sulfonic acid, phenylpentyl sulfonic acid, phenylhexyl sulfonic acid, phenylheptyl sulfonic acid, phenyloctyl sulfonic acid and phenylnonyl sulfonic acid; halogenated aralkyl sulfonic acids such as p-fluorophenylmethyl sulfonic acid, p-fluorophenylethyl sulfonic acid, p-fluorophenylpropyl sulfonic acid and p-fluorophenylbutyl sulfonic acid; and bicycloalkyl sulfonic acids such as camphor sulfonic acid.

The specific examples of the halosulfuric acid as the inorganic acid are, for example, fluorosulfuric acid, chlorosulfuric acid, bromosulfuric acid and iodosulfuric acid.

The specific examples of the perhalogenic acid are, for example, perfluoric acid, perchloric acid, perbromic acid and periodic acid.

The specific examples of the compound shown by the general formula [10] are, for example, tetrafluoroborate, tetrafluoroaluminate, tetrafluoroferrate, tetrafluorogallate, hexafluorophosphate, hexafluoroarsenate, hexafluoroantimonate, hexafluorobismuthate, hexafluorosilicate, hexafluoronickelate, hexafluorotitanate and hexafluorozirconate, and among others, hexafluorophosphate, hexafluoroarsenate and hexafluoroantimonate are preferable.

A preferable hybrid type onium salt shown by the general formula [1] includes, for example, one shown by the general formula [3];

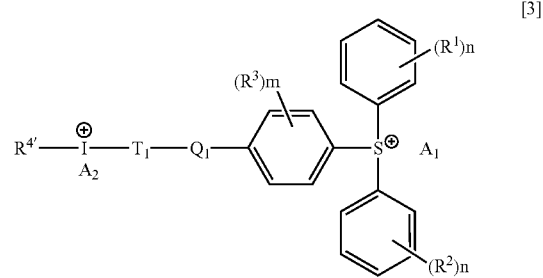

(wherein $R^{4'}$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted; and $R^1$ to $R^3$, $Q_1$, $T_1$, $A_1$, $A_2$, m and n are the same as described above), and one shown by the general formula [5];

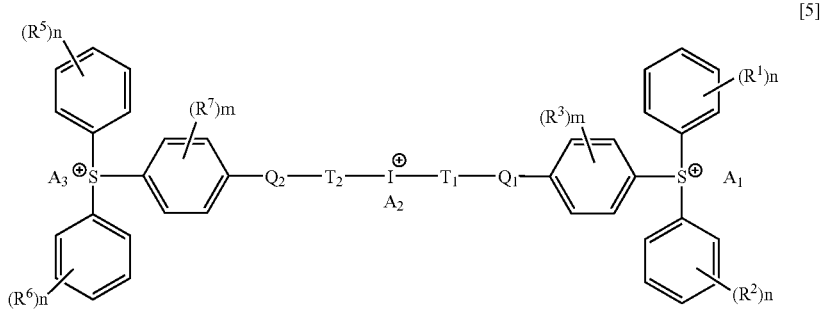

(wherein $R^1$ to $R^3$, $R^5$ to $R^7$, $Q_1$, $Q_2$, $T_1$, $T_2$, $A_1$ to $A_3$, m and n are the same as described above).

A more preferable hybrid type onium salt shown by the general formula [3] includes, for example, one shown by the general formula [4];

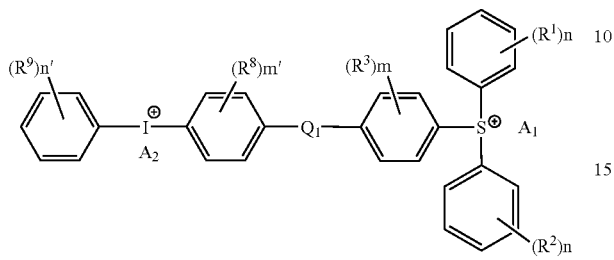

[4]

(wherein $R^8$ and $R^9$ are each independently a halogen atom, an alkyl group, a haloalkyl group, an aryl group, an alkoxy group, an aryloxy group, an alkylthio group, an arylthio group or an amino group which may be substituted; m' is an integer of 0 to 4; n' is an integer of 0 to 5; and $R^1$ to $R^3$, $Q_1$, $A_1$, $A_2$, m and n are the same as described above).

A more preferable hybrid type onium salt shown by the general formula [5] includes, for example, one shown by the general formula [6];

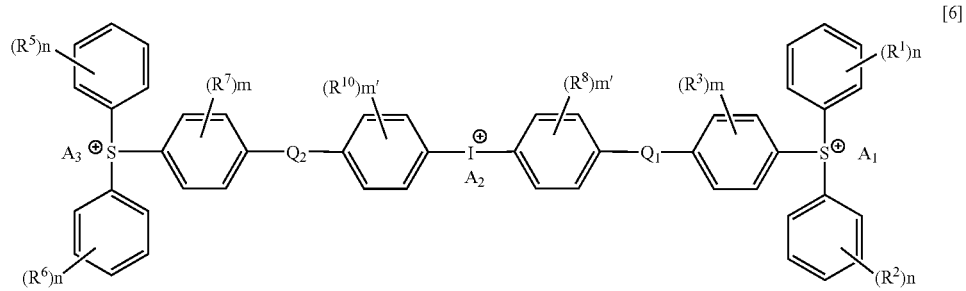

[6]

(wherein $R^{10}$ is a halogen atom, an alkyl group, a haloalkyl group, an aryl group, an alkoxy group, an aryloxy group, an alkylthio group, an arylthio group or an amino group which may be substituted; $R^1$ to $R^3$, $R^5$ to $R^7$, $R^8$, $Q_1$, $Q_2$, $A_1$ to $A_3$, m, m' and n are the same as described above), and further preferable one is specifically exemplified by, for example, one shown by the general formula [11];

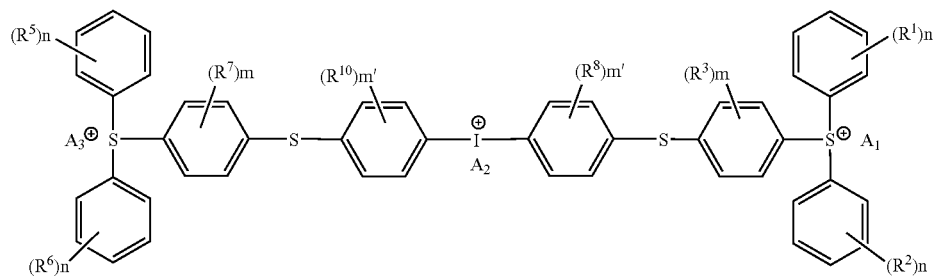

[11]

(wherein $R^1$ to $R^3$, $R^5$ to $R^8$, $R^{10}$, $A_1$ to $A_3$, m, m' and n are the same as described above), (corresponding to one wherein $Q_1$ and $Q_2$ in the general formula [6] are a sulfur atom), one shown by the general formula [12];

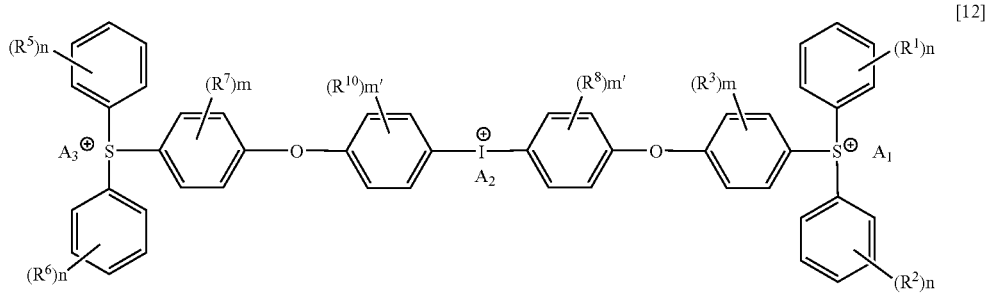

[12]

(wherein $R_1$ to $R^3$, $R^5$ to $R^8$, $R^{10}$, $A_1$ to $A_3$, m, m' and n are the same as described above), (corresponding to one wherein $Q_1$ and $Q_2$ in the general formula [6] are an oxygen atom), one shown by the general formula [13];

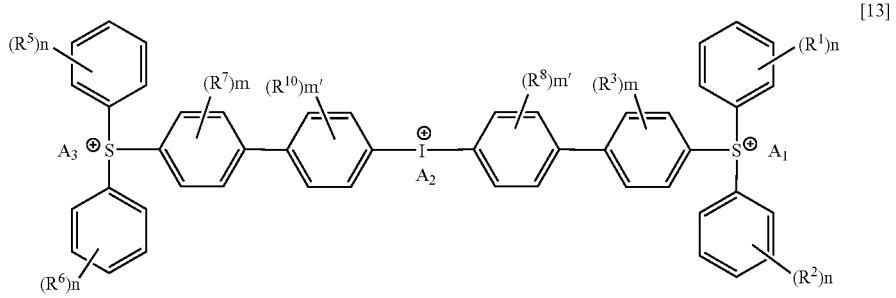

[13]

(wherein $R_1$ to $R^3$, $R^5$ to $R^8$, $R^{10}$, $A_1$ to $A_3$, m, m' and n are the same as described above), (corresponding to one wherein $Q_1$ and $Q_2$ in the general formula [6] are a direct-linkage) and one shown by the general formula [14];

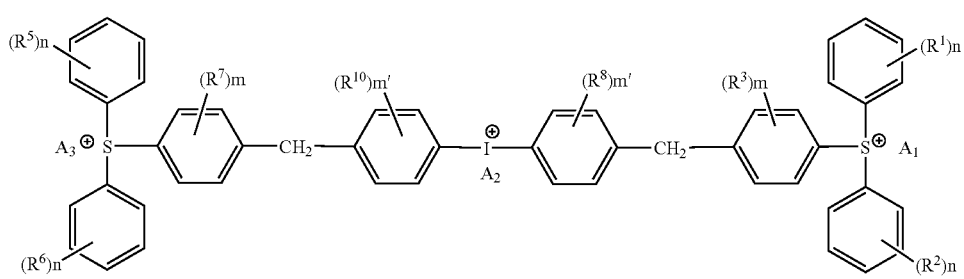

[14]

(wherein $R^1$ to $R^3$, $R^5$ to $R^8$, $R^{10}$, $A_1$ to $A_3$, m, m' and n are the same as described above), (corresponding to one wherein $Q_1$ and $Q_2$ in the general formula [6] are a methylene group) and the like.

Among these compounds, those shown by the general formulae [12] and [14] are particularly preferable.

In the general formula [3], the alkyl group, the alkenyl group, the aryl group or the aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, shown by $R^{4'}$ includes the same as examples of the halogen atom, the alkyl group, the alkenyl group, the aryl group or the aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, shown by $R^4$ in the above-described general formula [1].

In the general formulae [4], [6] and [11] to [14], the halogen atom, the alkyl group, the haloalkyl group, the aryl group, the alkoxy group, the aryloxy group, the alkylthio group, the arylthio group and the amino group which may be substituted, shown by $R^8$ to $R^{10}$ includes the same as examples of the halogen atom, the alkyl group, the haloalkyl group, the aryl group, the alkoxy group, the aryloxy group, the alkylthio group, the arylthio group and the amino group which may be substituted, shown by $R^1$ to $R^3$ and $R^5$ to $R^7$ in the general formulae [1], [2], [34], [35], [40] and [41].

m' is each independently an integer of generally 0 to 4, preferably 0 to 2 and more preferably 0.

n' is an integer of generally 0 to 5, preferably 0 to 3 and more preferably 0.

The preferable specific examples of the compound shown by the general formula [4] are, for example, 4-[4-(diphenylsulfonio)phenylthio]phenyl-phenyl iodonium bis(hexafluorophosphate), 4-[4-(diphenylsulfonio)phenoxy]phenyl-phenyl iodonium bis(hexafluorophosphate), 4-[4-(diphenylsulfonio)phenylmethyl]phenyl-phenyl iodonium bis(hexafluorophosphate), 4-[4-(diphenylsulfonio)(1,1'-biphenyl)-4'-yl]phenyl iodonium bis(hexafluorophosphate), 4-[4-(ditolylsulfonio)phenylthio]phenyl-phenyl iodonium bis(hexafluorophosphate), 4-[4-(ditolylsulfonio)phenoxy]phenyl-phenyl iodonium bis(hexafluorophosphate), 4-[4-(ditolylsulfonio)phenylmethyl]phenyl-phenyl iodonium bis(hexafluorophosphate), 4-[4-(diphenylsulfonio)phenylthio]phenyl-tolyl iodonium bis(hexafluorophosphate), 4-[4-(diphenylsulfonio)phenoxy]phenyl-tolyl iodonium bis(hexafluorophosphate), 4-[4-(diphenylsulfonio)phenylmethyl]phenyl-tolyl iodonium bis(hexafluorophosphate), 4-[4-(diphenylsulfonio)(1,1'-biphenyl)-4'-yl]-tolyl iodonium bis(hexafluorophosphate), 4-[4-(diphenylsulfonio)phenylthio]phenyl-xylyl iodonium bis(hexafluorophosphate), 4-[4-(diphenylsulfonio)phenylthio]phenyl-mesityl iodonium bis(hexafluorophosphate), 4-[4-(diphenylsulfonio)phenylthio]phenyl-phenyl iodonium bis(trifluoromethanesulfonate), 4-[4-(diphenylsulfonio)phenoxy]phenyl-phenyl iodonium bis(trifluoromethanesulfonate), 4-[4-(diphenylsulfonio)phenylmethyl]phenyl-phenyl iodonium bis(trifluoromethanesulfonate), 4-[4-(diphenylsulfonio)(1,1'-biphenyl)-4'-yl]-phenyl iodonium bis(trifluoromethanesulfonate), 4-[4-(ditolylsulfonio)phenylthio]phenyl-phenyl iodonium bis(trifluoromethanesulfonate), 4-[4-(ditolylsulfonio)phenoxy]phenyl-phenyl iodonium bis(trifluoromethanesulfonate), 4-[4-(ditolylsulfonio)phenylmethyl]phenyl-phenyl iodonium bis(trifluoromethanesulfonate), 4-[4-(diphenylsulfonio)phenylthio]phenyl-tolyl iodonium bis(trifluoromethanesulfonate), 4-[4-(diphenylsulfonio)phenoxy]phenyl-tolyl iodonium bis(trifluoromethanesulfonate), 4-[4-(diphenylsulfonio)phenylmethyl]phenyl-tolyl iodonium bis(trifluoromethanesulfonate), 4-[4-(diphenylsulfonio)(1,1'-biphenyl)-4'-yl]-tolyl iodonium bis(trifluoromethanesulfonate), 4-[4-(diphenylsulfonio)phenylthio]phenyl-xylyl iodonium bis(trifluoromethanesulfonate), 4-[4-(diphenylsulfonio)phenylthio]phenyl-mesityl iodonium bis(trifluoromethanesulfonate), 4-[4-(diphenylsulfonio)phenylthio]phenyl-phenyl iodonium bis(nonafluorobutanesulfonate), 4-[4-(diphenylsulfonio)phenoxy]phenyl-phenyl iodonium bis(nonafluorobutanesulfonate), 4-[4-(diphenylsulfonio)phenylmethyl]phenyl-phenyl iodonium bis(nonafluorobutanesulfonate), 4-[4-(diphenylsulfonio)(1,1'-biphenyl)-4'-yl]-phenyl iodonium bis(nonafluorobutanesulfonate), 4-[4-(ditolylsulfonio)phenylthio]phenyl-phenyl iodonium bis(nonafluorobutanesulfonate), 4-[4-(ditolylsulfonio)phenoxy]phenyl-phenyl iodonium bis(nonafluorobutanesulfonate), 4-[4-(ditolylsulfonio)phenylmethyl]phenyl-phenyl iodonium bis(nonafluorobutanesulfonate), 4-[4-(diphenylsulfonio)phenylthio]phenyl-tolyl iodonium bis(nonafluorobutanesulfonate), 4-[4-(diphenylsulfonio)phenoxy]phenyl-tolyl iodonium bis(nonafluorobutanesulfonate), 4-[4-(diphenylsulfonio)phenylmethyl]phenyl-tolyl iodonium bis(nonafluorobutanesulfonate), 4-[4-(diphenylsulfonio)(1,1'-biphenyl)-4'-yl]-tolyl iodonium bis(nonafluorobutanesulfonate), 4-[4-(diphenylsulfonio)phenylthio]phenyl-xylyl iodonium bis(nonafluorobutanesulfonate), 4-[4-(diphenylsulfonio)phenylthio]phenyl-mesityl iodonium bis(nonafluorobutanesulfonate), 4-[4-(diphenylsulfonio)phenylthio]phenyl-phenyl iodonium bis(pentafluorobenzenesulfonate), 4-[4-(diphenylsulfonio)phenoxy]phenyl-phenyl iodonium bis(pentafluorobenzenesulfonate), 4-[4-(diphenylsulfonio)phenylmethyl]phenyl-phenyl iodonium bis(pentafluorobenzenesulfonate), 4-[4-(diphenylsulfonio)(1,1'-biphenyl)-4'-yl]-phenyl iodonium bis(pentafluorobenzenesulfonate), 4-[4-(ditolylsulfonio)phenylthio]phenyl-phenyl iodonium bis(pentafluorobenzenesulfonate), 4-[4-(ditolylsulfonio)phenoxy]phenyl-phenyl iodonium bis(pentafluorobenzenesulfonate), 4-[4-(ditolylsulfonio)phenylmethyl]phenyl-phenyl iodonium bis(pentafluorobenzenesulfonate), 4-[4-(diphenylsulfonio)phenylthio]phenyl-tolyl iodonium bis(pentafluorobenzenesulfonate), 4-[4-(diphenylsulfonio)phenoxy]phenyl-tolyl -iodonium bis(pentafluorobenzenesulfonate), 4-[4-(diphenylsulfonio)phenylmethyl]phenyl-tolyl iodonium bis(pentafluorobenzenesulfonate), 4-[4-(diphenylsulfonio)(1,1'-biphenyl)-4'-yl]-tolyl iodonium bis(pentafluorobenzenesulfonate), 4-[4-(diphenylsulfonio)phenylthio]phenyl-xylyl iodonium bis(pentafluorobenzenesulfonate), 4-[4-(diphenylsulfonio)phenylthio]phenyl-mesityl iodonium bis(pentafluorobenzenesulfonate), 4-[4-(diphenylsulfonio)phenylthio]phenyl-phenyl iodonium bis(perchlorate), 4-[4-(diphenylsulfonio)phenoxy]phenyl-phenyl iodonium bis(perchlorate), 4-[4-(diphenylsulfonio)phenylmethyl]phenyl-phenyl iodonium bis(perchlorate), 4-[4-(diphenylsulfonio)(1,1'-biphenyl)-4'-yl]phenyl iodonium bis(perchlorate), 4-[4-(ditolylsulfonio)phenylthio]phenyl-phenyl iodonium bis(perchlorate), 4-[4-(ditolylsulfonio)phenoxy]phenyl-phenyl iodonium bis(perchlorate), 4-[4-(ditolylsulfonio)phenylmethyl]phenyl-phenyl iodonium bis(perchlorate), 4-[4-(diphenylsulfonio)phenylthio]phenyl-tolyl iodonium bis(perchlorate), 4-[4-(diphenylsulfonio)phenoxy]phenyl-tolyl iodonium bis(perchlorate), 4-[4-(diphenylsulfonio)phenylmethyl]phenyl-tolyl iodonium bis(perchlorate), 4-[4-(diphenylsulfonio)(1,1'-biphenyl)-4'-yl]tolyl iodonium bis(perchlorate), 4-[4-(diphenylsulfonio)phenylthio]phenyl-xylyl iodonium bis(perchlorate), 4-[4-(diphenylsulfonio)-phenylthio]phenyl-mesityl iodonium bis(perchlorate), 4-[4-(diphenylsulfonio)phenylthio]phenyl-phenyl iodonium bis{tetrakis(pentafluorophenyl)borate}, 4-[4-(diphenylsulfonio)phenoxy]phenyl-phenyl iodonium bis{tetrakis(pentafluorophenyl)borate}, 4-[4-(diphenylsulfonio)phenylmethyl]phenyl-phenyl iodonium bis{tetrakis(pentafluorophenyl)borate}, 4-[4-(diphenylsulfonio)(1,1'-biphenyl)-4'-yl]-phenyl iodonium bis{tetrakis(pentafluorophenyl)borate}, 4-[4-(ditolylsulfonio)phenylthio]phenyl-phenyl iodonium bis{tetrakis(pentafluorophenyl)borate}, 4-[4-(ditolylsulfonio)phenoxy]phenyl-phenyl iodonium bis{tetrakis(pentafluorophenyl)

borate}, 4-[4-(ditolylsulfonio)phenylmethyl]phenyl-phenyl iodonium bis{tetrakis(pentafluorophenyl)borate}, 4-[4-(diphenylsulfonio)phenylthio]phenyl-tolyl iodonium bis{tetrakis(pentafluorophenyl)borate}, 4-[4-(diphenylsulfonio)phenoxy]phenyl-tolyl iodonium bis{tetrakis(pentafluorophenyl)borate}, 4-[4-(diphenylsulfonio)phenylmethyl]phenyl-tolyl iodonium bis{tetrakis(pentafluorophenyl)borate}, 4-[4-(diphenylsulfonio)(1,1'-biphenyl)-4'-yl]-tolyl iodonium bis{tetrakis(pentafluorophenyl)borate}, 4-[4-(diphenylsulfonio)phenylthio]phenyl-xylyl iodonium bis{tetrakis(pentafluorophenyl)borate} and 4-[4-(diphenylsulfonio)phenylthio]phenyl-mesityl iodonium bis{tetrakis(pentafluorophenyl)borate}, and among others, for example, 4-[4-(diphenylsulfonio)phenylthio]phenyl-phenyl iodonium bis(hexafluorophosphate), 4-[4-(diphenylsulfonio)phenoxy]phenyl-phenyl iodonium bis(hexafluorophosphate), 4-[4-(diphenylsulfonio)phenylmethyl]phenyl-phenyl iodonium bis(hexafluorophosphate), 4-[4-(diphenylsulfonio)(1,1'-biphenyl)-4'-yl]-phenyl iodonium bis(hexafluorophosphate), 4-[4-(diphenylsulfonio)phenylthio]phenyl-phenyl iodonium bis(trifluoromethanesulfonate), 4-[4-(diphenylsulfonio)phenoxy]phenyl-phenyl iodonium bis(trifluoromethanesulfonate), 4-[4-(diphenylsulfonio)phenylmethyl]phenyl-phenyl iodonium bis(trifluoromethanesulfonate), 4-[4-(diphenylsulfonio)(1,1'-biphenyl)-4'-yl]-phenyl iodonium bis(trifluoromethanesulfonate), 4-[4-(diphenylsulfonio)phenylthio]phenyl-phenyl iodonium bis(nonafluorobutanesulfonate), 4-[4-(diphenylsulfonio)phenoxy]phenyl-phenyl iodonium bis(nonafluorobutanesulfonate), 4-[4-(diphenylsulfonio)phenylmethyl]phenyl-phenyl iodonium bis(nonafluorobutanesulfonate), 4-[4-(diphenylsulfonio)(1,1'-biphenyl)-4'-yl]-phenyl iodonium bis(nonafluorobutanesulfonate), 4-[4-(diphenylsulfonio)phenylthio]phenyl-phenyl iodonium bis(pentafluorobenzenesulfonate), 4-[4-(diphenylsulfonio)phenoxy]phenyl-phenyl iodonium bis(pentafluorobenzenesulfonate), 4-[4-(diphenylsulfonio)phenylmethyl]phenyl-phenyl iodonium bis(pentafluorobenzenesulfonate) and 4-[4-(diphenylsulfonio)(1,1'-biphenyl)-4'-yl]-phenyl iodonium bis(pentafluorobenzenesulfonate) are more preferable.

The preferable specific examples of the compound shown by the general formula [11] are, for example, bis{4-[4-(diphenylsulfonio)phenylthio]phenyl}iodonium tris(hexafluorophosphate), bis{4-[4-(ditolylsulfonio)phenylthio]phenyl}iodonium tris(hexafluorophosphate), bis{4[4-(dixylylsulfonio)phenylthio]phenyl}iodonium tris(hexafluorophosphate), bis{4-[4-(dimesitylsulfonio)phenylthio]phenyl}iodonium tris(hexafluorophosphate), bis{4-[4-(diphenylsulfonio)phenylthio]phenyl}iodonium tris(trifluoromethanesulfonate), bis{4-[4-(ditolylsulfonio)phenylthio]phenyl}iodonium tris(trifluoromethanesulfonate), bis{4-[4-(dixylylsulfonio)phenylthio]phenyl}iodonium tris(trifluoromethanesulfonate), bis{4-[4-(dimesitylsulfonio)phenylthio]phenyl}iodonium tris(trifluoromethanesulfonate), bis{4-[4-(diphenylsulfonio)phenylthio]phenyl}iodonium tris(nonafluorobutanesulfonate), bis{4-[4-(ditolylsulfonio)phenylthio]phenyl}iodonium tris(nonafluorobutanesulfonate), bis{4-[4-(dixylylsulfonio)phenylthio]phenyl}iodonium tris(nonafluorobutanesulfonate), bis{4-[4-(dimesitylsulfonio)phenylthio]phenyl}iodonium tris(nonafluorobutanesulfonate), bis{4-[4-(diphenylsulfonio)phenylthio]phenyl}iodonium tris(pentafluorobenzenesulfonate), bis{4-[4-(ditolylsulfonio)phenylthio]phenyl}iodonium tris(pentafluorobenzenesulfonate), bis{4-[4-(dixylylsulfonio)phenylthio]phenyl}iodonium tris(pentafluorobenzenesulfonate), bis{4-[4-(dimesitylsulfonio)phenylthio]phenyl}iodonium tris(pentafluorobenzenesulfonate), bis{4-[4-(diphenylsulfonio)phenylthio]phenyl}iodonium tris(perchlorate), bis{4-[4-(ditolylsulfonio)phenylthio]phenyl}iodonium tris(perchlorate), bis{4-[4-(dixylylsulfonio)phenylthio]phenyl}iodonium tris(perchlorate), bis{4-[4-(dimesitylsulfonio)phenylthio]phenyl}iodonium tris(perchlorate), bis{4-[4-(diphenylsulfonio)phenylthio]phenyl}iodonium tris{tetrakis(pentafluorophenyl)borate}, bis{4-[4-(ditolylsulfonio)phenylthio]phenyl}iodonium tris{tetrakis(pentafluorophenyl)borate}, bis{4-[4-(dixylylsulfonio)phenylthio]phenyl}iodonium tris{tetrakis(pentafluorophenyl)borate} and bis{4-[4-(dimesitylsulfonio)phenylthio]phenyl}iodonium tris{tetrakis(pentafluorophenyl)borate}, and among others, for example, bis{4-[4-(diphenylsulfonio)phenylthio]phenyl}iodonium tris(hexafluorophosphate), bis{4-[4-(diphenylsulfonio)phenylthio]phenyl}iodonium tris(trifluoromethanesulfonate), bis{4-[4-(diphenylsulfonio)phenylthio]phenyl}iodonium tris(nonafluorobutanesulfonate) and bis{4-[4-(diphenylsulfonio)phenylthio]phenyl}iodonium tris(pentafluorobenzenesulfonate) are more preferable.

The preferable specific examples of the compound shown by the general formula [12] are, for example, bis{4-[4-(diphenylsulfonio)phenoxy]phenyl}iodonium tris(hexafluorophosphate), bis{4-[4-(ditolylsulfonio)phenoxy]phenyl}iodonium tris(hexafluorophosphate), bis{4-[4-(dixylylsulfonio)phenoxy]phenyl}iodonium tris(hexafluorophosphate), bis{4-[4-(dimesitylsulfonio)phenoxy]phenyl}iodonium tris(hexafluorophosphate), bis{4-[4-(diphenylsulfonio)phenoxy]phenyl}iodonium tris(trifluoromethanesulfonate), bis{4-[4-(ditolylsulfonio)phenoxy]phenyl}iodonium tris(trifluoromethanesulfonate), bis{4-[4-(dixylylsulfonio)phenoxy]phenyl}iodonium tris(trifluoromethanesulfonate), bis{4-[4-(dimesitylsulfonio)phenoxy]phenyl}iodonium tris(trifluoromethanesulfonate), bis{4-[4-(diphenylsulfonio)phenoxy]phenyl}iodonium tris(nonafluorobutanesulfonate), bis{4-[4-(ditolylsulfonio)phenoxy]phenyl}iodonium tris(nonafluorobutanesulfonate), bis{4-[4-(dixylylsulfonio)phenoxy]phenyl}iodonium tris(nonafluorobutanesulfonate), bis{4-[4-(dimesitylsulfonio)phenoxy]phenyl}iodonium tris(nonafluorobutanesulfonate), bis{4-[4-(diphenylsulfonio)phenoxy]phenyl}iodonium tris(pentafluorobenzenesulfonate), bis{4-[4-(ditolylsulfonio)phenoxy]phenyl}iodonium tris(pentafluorobenzenesulfonate), bis{4-[4-(dixylylsulfonio)phenoxy]phenyl}iodonium tris(pentafluorobenzenesulfonate), bis{4-[4-(dimesitylsulfonio)phenoxy]phenyl}iodonium tris(pentafluorobenzenesulfonate), bis{4-[4-(diphenylsulfonio)phenoxy]phenyl}iodonium tris(perchlorate), bis{4-[4-(ditolylsulfonio)phenoxy]phenyl}iodonium tris(perchlorate), bis{4-[4-(dixylylsulfonio)phenoxy]phenyl}iodonium tris(perchlorate), bis{4-[4-(dimesitylsulfonio)phenoxy]phenyl}iodonium tris (perchlorate), bis{4-[4-(diphenylsulfonio)phenoxy]phenyl}iodonium tris{tetrakis(pentafluorophenyl)borate}, bis{4-[4-(ditolylsulfonio)phenoxy]phenyl}iodonium tris{tetrakis(pentafluorophenyl)borate}, bis{4-[4-(dixylylsulfonio)phenoxy]phenyl}iodonium tris{tetrakis(pentafluorophenyl)borate} and bis{4-[4-(dimesitylsulfonio)phenoxy]phenyl}iodonium tris{tetrakis(pentafluorophenyl)borate}, and among others, bis{4-[4-(diphenylsulfonio)phenoxy]phenyl}iodonium tris(hexafluorophosphate), bis{4-[4-(diphenylsulfonio)phenoxy]phenyl}iodonium tris(trifluoromethanesulfonate), bis{4-[4-(diphenylsulfonio)phenoxy]phenyl}iodonium tris(nonafluorobutanesulfonate) and bis{4-[4-(diphenylsulfonio)phenoxy]phenyl}iodonium tris(pentafluorobenzenesulfonate) are more preferable.

The preferable specific examples of the compound shown by the general formula [13] are, for example, bis[4-(diphenylsulfonio)(1,1'-biphenyl)-4'-yl]iodonium tris(hexafluorophosphate), bis[4-(ditolylsulfonio)(1,1'-biphenyl)-4'-yl]iodonium tris(hexafluorophosphate), bis[4-(dixylylsulfonio)(1,1'-biphenyl)-4'-yl]iodonium tris(hexafluorophosphate), bis[4-(dimesitylsulfonio)(1,1'-biphenyl)-4'-yl]iodonium tris(hexafluorophosphate), bis[4-(diphenylsulfonio)(1,1'-biphenyl)-4'-yl]iodonium tris(trifluoromethanesulfonate), bis[4-(ditolylsulfonio)(1,1'-biphenyl)-4'-yl]iodonium tris(trifluoromethanesulfonate), bis[4-(dixylylsulfonio)(1,1'-biphenyl)-4'-yl]iodonium tris(trifluoromethanesulfonate), bis[4-(dimesitylsulfonio)(1,1'-biphenyl)-4'-yl]iodonium tris(trifluoromethanesulfonate), bis[4-(diphenylsulfonio)(1,1'-biphenyl)-4'-yl]iodonium tris(nonafluorobutanesulfonate), bis[4-(ditolylsulfonio)(1,1'-biphenyl)-4'-yl]iodonium tris(nonafluorobutanesulfonate), bis[4-(dixylylsulfonio)(1,1'-biphenyl)-4'-yl]iodonium tris(nonafluorobutanesulfonate), bis[4-(dimesitylsulfonio)(1,1'-biphenyl)-4'-yl]iodonium tris(nonafluorobutanesulfonate), bis[4-(diphenylsulfonio)(1,1'-biphenyl)-4'-yl]iodonium tris(pentafluorobenzenesulfonate), bis[4-(ditolylsulfonio)(1,1'-biphenyl)-4'-yl]iodonium tris(pentafluorobenzenesulfonate), bis[4-(dixylylsulfonio(1,1'-biphenyl)-4'-yl]iodonium tris(pentafluorobenzenesulfonate), bis[4-(dimesitylsulfonio)(1,1'-biphenyl)-4'-yl]iodonium tris(pentafluorobenzenesulfonate), bis[4-(diphenylsulfonio)(1,1'-biphenyl)-4'-yl]iodonium tris(perchlorate), bis[4-(ditolylsulfonio)(1,1'-biphenyl)-4'-yl]iodonium tris(perchlorate), bis[4-(dixylylsulfonio)(1,1'-biphenyl)-4'-yl]iodonium tris(perchlorate), bis[4-(dimesitylsulfonio)(1,1'-biphenyl)-4'-yl]iodonium tris(perchlorate), bis[4-(diphenylsulfonio)(1,1'-biphenyl)-4'-yl]iodonium tris{tetrakis(pentafluorophenyl)borate}, bis[4-(ditolylsulfonio)(1,1'-biphenyl)-4'-yl]iodonium tris{tetrakis(pentafluorophenyl)borate}, bis[4-(dixylylsulfonio)(1,1'-biphenyl)-4'-yl]iodonium tris{tetrakis(pentafluorophenyl)borate} and bis[4-(dimesitylsulfonio)(1,1'-biphenyl)-4'-yl]iodonium tris{tetrakis(pentafluorophenyl)borate}, and among others, bis[4-(diphenylsulfonio)(1,1'-biphenyl)-4'-yl]iodonium tris(hexafluorophosphate), bis[4-(diphenylsulfonio)(1,1'-biphenyl)-4'-yl]iodonium tris(trifluoromethanesulfonate), bis[4-(diphenylsulfonio)(1,1'-biphenyl)-4'-yl]iodonium tris(nonafluorobutanesulfonate) and bis[4-(diphenylsulfonio)(1,1'-biphenyl)-4'-yl]iodonium tris(pentafluorobenzenesulfonate) are more preferable.

The preferable specific examples of the compound shown by the general formula [14] are, for example, bis{4-[4-(diphenylsulfonio)phenylmethyl]phenyl}iodonium tris(hexafluorophosphate), bis{4-[4-(ditolylsulfonio)phenylmethyl]phenyl}iodonium tris(hexafluorophosphate), bis{4-[4-(dixylylsulfonio)phenylmethyl]phenyl}iodonium tris(hexafluorophosphate), bis{4-[4-(dimesitylsulfonio)phenylmethyl]phenyl}iodonium tris(hexafluorophosphate), bis{4-[4-(diphenylsulfonio)phenylmethyl]phenyl}iodonium tris(trifluoromethanesulfonate), bis{4-[4-(ditolylsulfonio)phenylmethyl]phenyl}iodonium tris(trifluoromethanesulfonate), bis{4-[4-(dixylylsulfonio)phenylmethyl]phenyl}iodonium tris(trifluoromethanesulfonate), bis{4-[4-(dimesitylsulfonio)phenylmethyl]phenyl}iodonium tris(trifluoromethanesulfonate), bis{4-[4-(diphenylsulfonio)phenylmethyl]phenyl}iodonium tris(nonafluorobutanesulfonate), bis{4-[4-(ditolylsulfonio)phenylmethyl]phenyl}iodonium tris(nonafluorobutanesulfonate), bis{4-[4-(dixylylsulfonio)phenylmethyl]phenyl}iodonium tris(nonafluorobutanesulfonate), bis{4-[4-(dimesitylsulfonio)phenylmethyl]phenyl}iodonium tris(nonafluorobutanesulfonate), bis{4-[4-(diphenylsulfonio)phenylmethyl]phenyl}iodonium tris(pentafluorobenzenesulfonate), bis{4-[4-(ditolylsulfonio)phenylmethyl]phenyl}iodonium tris(pentafluorobenzenesulfonate), bis{4-[4-(dixylylsulfonio)phenylmethyl]phenyl}iodonium tris(pentafluorobenzenesulfonate), bis{4-[4-(dimesitylsulfonio)phenylmethyl]phenyl}iodonium tris(pentafluorobenzenesulfonate), bis{4-[4-(diphenylsulfonio)phenylmethyl]phenyl}iodonium tris(perchlorate), bis{4-[4-(ditolylsulfonio)phenylmethyl]phenyl}iodonium tris(perchlorate), bis{4-[4-(dixylylsulfonio)phenylmethyl]phenyl}iodonium tris(perchlorate), bis{4-[4-(dimesitylsulfonio)phenylmethyl]phenyl}iodonium tris(perchlorate), bis{4-[4-(diphenylsulfonio)phenylmethyl]phenyl}iodonium tris{tetrakis(pentafluorophenyl)borate}, bis{4-[4-(ditolylsulfonio)phenylmethyl]phenyl}iodonium tris{tetrakis(pentafluorophenyl)borate}, bis{4-[4-(dixylylsulfonio)phenylmethyl]phenyl}iodonium tris{tetrakis(pentafluorophenyl)borate} and bis{4-[4-(dimesitylsulfonio)phenylmethyl]phenyl}iodonium tris{tetrakis(pentafluorophenyl)borate}, and among others, bis{4-[4-(diphenylsulfonio)phenylmethyl]phenyl}iodonium tris(hexafluorophosphate), bis{4-[4-(diphenylsulfonio)phenylmethyl]phenyl}iodonium tris(trifluoromethanesulfonate), bis{4-[4-(diphenylsulfonio)phenylmethyl]phenyl}iodonium tris(nonafluorobutanesulfonate) and bis{4-[4-(diphenylsulfonio)phenylmethyl]phenyl}iodonium tris(pentafluorobenzenesulfonate) are more preferable.

The hybrid type onium salt shown by the general formula [1] can be obtained by first synthesizing a sulfonium salt shown by the following general formula [20], as an intermediate, followed by preparing an iodonium salt thereof.

The sulfonium salt shown by the general formula [20] can be synthesized, for example, by the following methods [A], [B], [C] and the like.

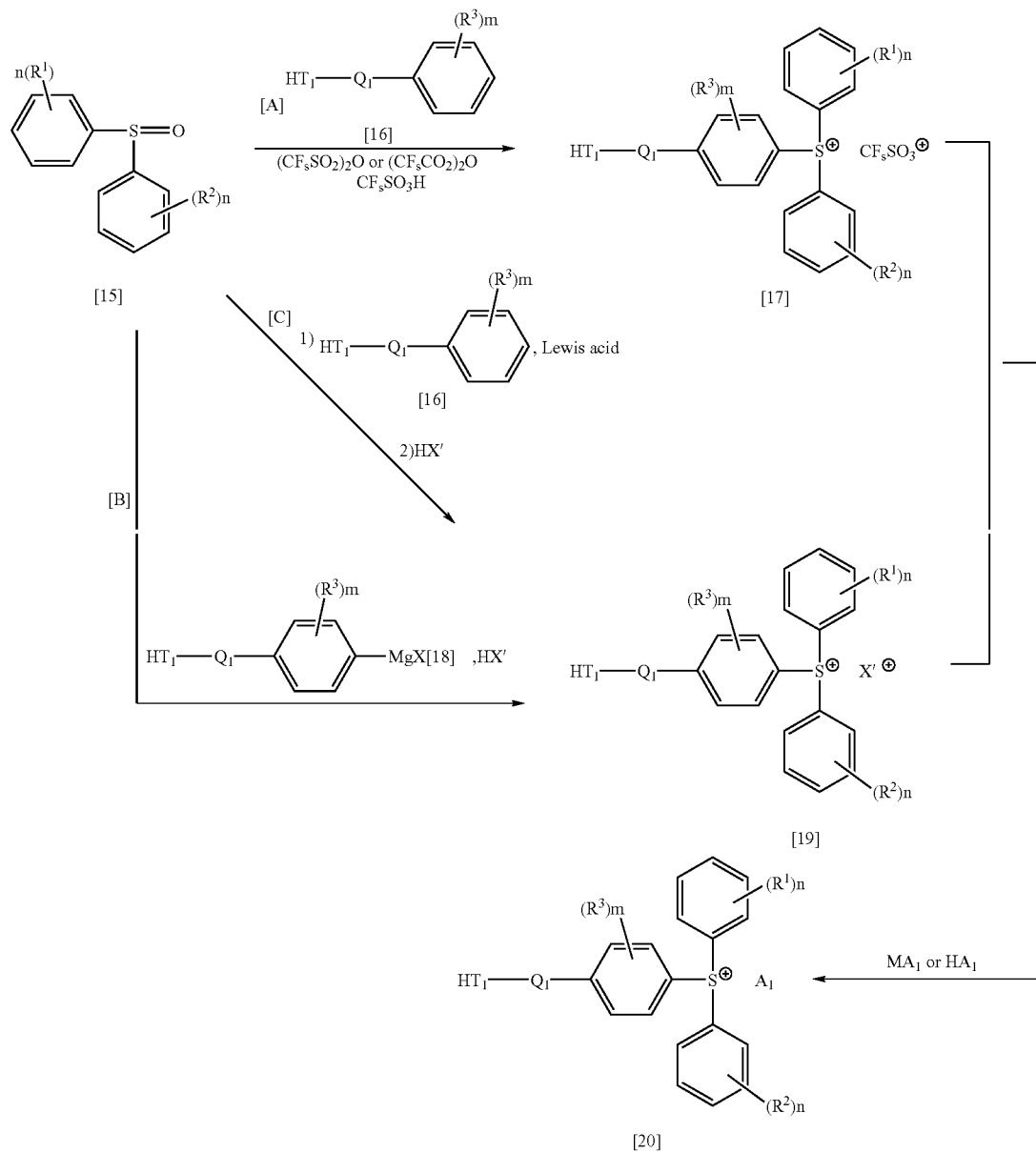

(wherein X and X' are each independently a halogen atom; M is a metal atom; $R^1$ to $R^3$, $Q_1$, $T_1$, $A_1$, m and n are the same as described above).

The halogen atom shown by X and X' includes, for example, a fluorine atom, a chlorine atom, a bromine atom and an iodine atom.

The metal atom shown by M includes, for example, a lithium atom, a sodium atom, a potassium atom, a rubidium atom, a silver atom and a cesium atom, and among others, a sodium atom and a potassium atom are preferable.

The compound shown by the general formula [16] may be a commercial product or one suitably synthesized in accordance with a common method.

The Grignard reagent shown by the general formula [18] may be one suitably synthesized in accordance with a common method.

Namely, in the method [A], a sulfoxide shown by the general formula [15], synthesized by a common method (for example, see Ber., 23, 1844 (1890) and J. Chem. Soc.(C), 2424 (1969)) is dissolved in a solvent such as ethers including ethyl ether, isopropyl ether, tetrahydrofuran and 1,2-dimethoxyethane; hydrocarbons including hexane and heptane; or aromatic hydrocarbons including benzene and nitrobenzene; or a mixed solvent consisting of the above solvent and halogenated hydrocarbons including methylene chloride, methylene bromide, 1,2-dichloroethane and chloroform, and a compound shown by the general formula [16] in an amount of 1 to 10 mole parts, trifluoromethanesulfonic anhydride in an amount of 1 to 3 mole parts or trifluoromethanesulfonic acid in an amount of 1 to 3 mole parts and trifluoroacetic anhydride in an amount of 1 to 3 mole parts, relative to 1 mole part of the sulfoxide shown by the general formula [15] are added thereto at −80 to 30° C., followed by allowing a reaction to take place at −80 to 30° C. for 0.5 to 10 hours with stirring, whereby the compound shown by the general formula [17] is obtained. The obtained compound is then treated with an ion exchange resin, followed by reacting with a solution of $MA_1$ or $HA_1$ to obtain a sulfonium salt having a desired counter anion $A_1$ shown by the general formula [20].

In the method [B], a compound shown by the general formula [15] is dissolved in ethers such as ethyl ether, isopropyl ether, tetrahydrofuran and 1,2-dimethoxy ethane, or a mixed solvent consisting of the above ethers and halogenated hydrocarbons such as methylene chloride, methylene bromide, 1,2-dichloroethane and chloroform and aromatic hydrocarbons such as benzene, toluene and xylene, and a Grignard reagent shown by the general formula [18] in an amount of 0.5 to 3 mole parts relative to 1 mole part of the compound shown by the general formula [15] is added thereto, if necessary, in the presence of a catalyst such as trimethylsilyl triflate or, trimethylsilyl chloride, at −70 to 50° C., followed by allowing a reaction to take place at −70 to 50° C. for 0.5 to 10 hours with stirring. After completion of the reaction, the reaction solution is treated with an aqueous solution of hydrohalic acid (HX') such as an aqueous solution of hydrobromic acid, hydrochloric acid or hydroiodic acid to obtain a compound shown by the general formula [19]. The resulting compound is then treated with an ion exchange resin, followed by reacting with a solution of $MA_1$ or $HA_1$ to obtain a sulfonium salt having a desired counter anion $A_1$ shown by the general formula [20].

In the method [C], a compound shown by the general formula [15] is reacted with a compound shown by the general formula [16] in an amount of 1 to 50 mole parts and Lewis acid in an amount of 1 to 10 mole parts, relative to 1 mole part of said compound at −20 to 180° C. for 0.5 to 24 hours with stirring, followed by treating with an aqueous solution of hydrohalic acid (HX') such as an aqueous solution of hydrobromic acid, hydrochloric acid or hydroiodic acid to obtain a compound shown by the general formula [19]. The resulting compound is then treated with an ion exchange resin, followed by reacting with a solution of $MA_1$ or $HA_1$ to obtain a sulfonium salt having a desired counter anion $A_1$ shown by the general formula [20].

Further, the hybrid type onium salt of the present invention, shown by the general formula [1] can be synthesized from the sulfonium salt shown by the above-described general formula [20], by the following methods [D], [E] and the like. Here, a method for manufacturing a hybrid type onium salt of the present invention, wherein a plurality of counter anions thereof is the same, is shown.

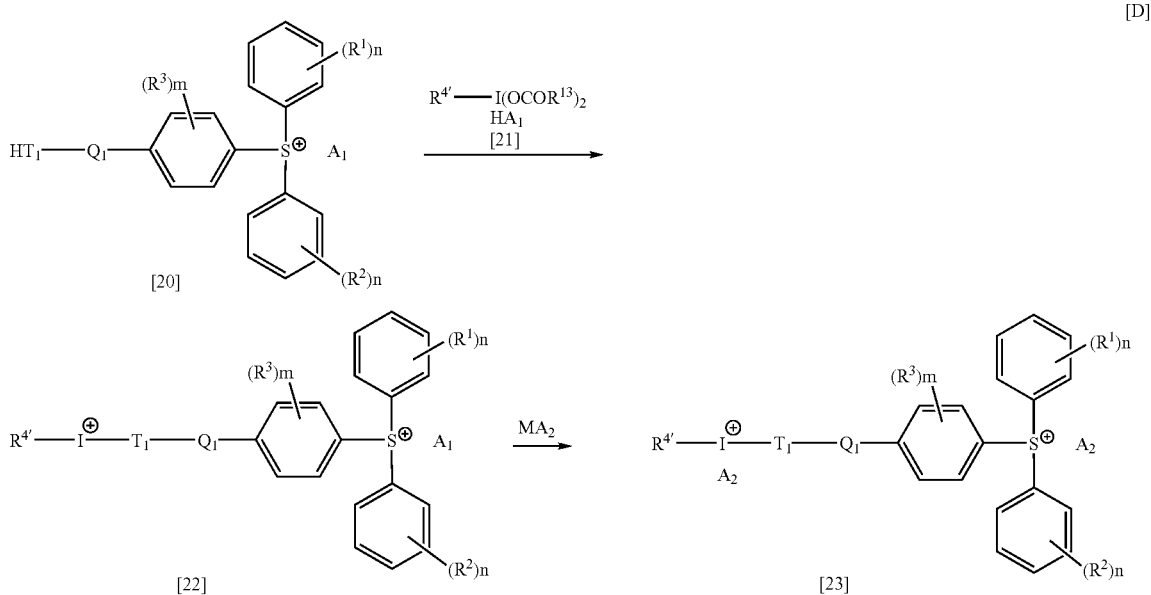

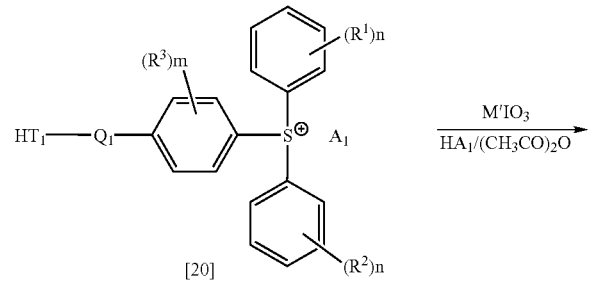

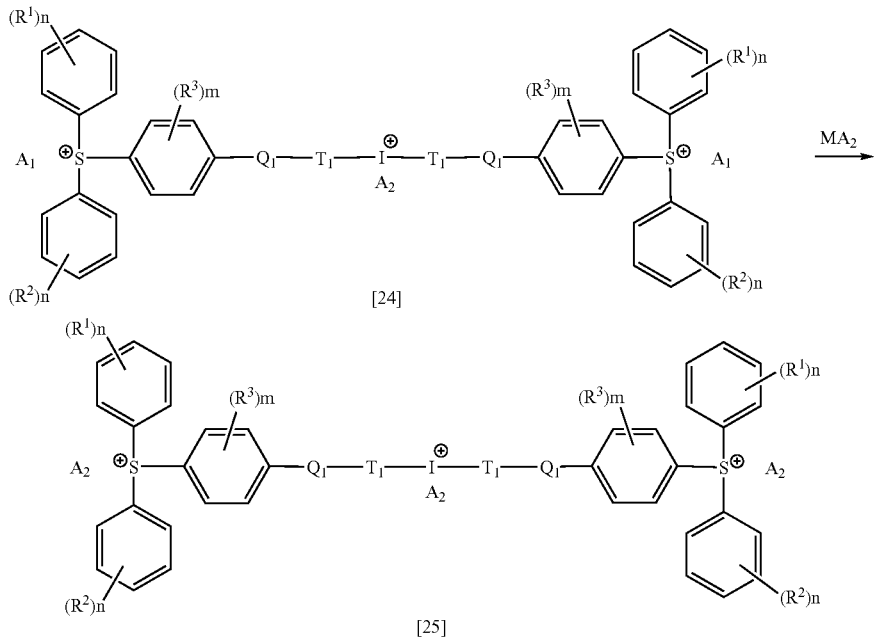

(wherein $R^{13}$ is a lower alkyl group or a lower haloalkyl group; M' is a metal atom; $R^1$ to $R^3$, $R^{4t}$, $Q_1$, $T_1$, $A_1$, $A_2$, M, m and n are the same as described above).

In the general formula [21], the lower haloalkyl group shown by $R^{13}$ may be straight chained, branched or cyclic, and includes one having generally 1 to 6 carbon atoms, preferably 1 to 3 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 3-methylpentyl group, a 1,2-dimethylbutyl group, a 2,2-dimethylbutyl group, a 1-ethylbutyl group and a 2-ethylbutyl group.

The lower haloalkyl group shown by $R^{13}$ includes one, wherein a part or all of hydrogen atoms of the lower alkyl group shown by the above-described $R^{13}$ are substituted by a halogen atom (e.g. a fluorine atom, a chlorine atom, a bromine atom and an iodine atom).

The metal atom shown by M' includes, for example, a lithium atom, a sodium atom, a potassium atom, a rubidium atom and a cesium atom, and among others, a sodium atom and a potassium atom are preferable.

The compound shown by the general formula [21] may be a commercial product or a suitably synthesized one according to common solutions.

Namely, in the method [D], a sulfonium salt compound shown by the general formula [20], synthesized by the above-described methods [A], [B] and [C], is dissolved in carboxylic anhydrides such as acetic anhydride and propionic anhydride or a mixed solvent consisting of the carboxylic anhydrides and halogenated hydrocarbons such as methylene chloride, methylene bromide, 1,2-dichloroethane and chloroform and aromatic hydrocarbons such as benzene, toluene and xylene, and a compound shown by the general formula [21] in an amount of 1 to 10 mole parts relative to 1 mole part of said compound is added thereto at −80 to 30° C., then a compound ($HA_1$) in an amount of 1 to 10 mole parts is further added dropwise thereto at −80 to 30° C. for 0.5 to 10 hours, followed by allowing a reaction to take place at −80 to 30° C. for 0.5 to 10 hours with stirring, thereby a desired compound shown by the general formula [22] is obtained. Then the obtained compound shown by the general formula [22] is dissolved in halogenated hydrocarbons such as methylene chloride, methylene bromide, 1,2-dichloroethane and chloroform, and an aqueous solution of a compound ($HA_2$) in an amount of 1 to 10 mole parts relative to 1 mole part of said compound is added thereto, followed by allowing a reaction to take place at 0 to 30° C. for 0.5 to 10 hours with stirring, to obtain an onium salt having a counter anion $A_2$, shown by the general formula [23].

In the method [E], a compound shown by the general formula [20] is dissolved in carboxylic anhydrides such as acetic anhydride and propionic anhydride or a mixed solvent consisting the carboxylic anhydrides and halogenated hydrocarbons such as methylene chloride, methylene bromide, 1,2-dichloroethane and chloroform and aromatic hydrocarbons such as benzene, toluene and xylene, and iodate salts ($M'IO_3$) such as lithium iodate, sodium iodate and potassium iodate in an amount of 0.4 to 0.6 mole parts relative to 1 mole part of said compound is added thereto at −70 to 30° C., then concentrated sulfuric acid in an amount of 1 to 10 mole parts or a mixed acid consisting of the said concentrated sulfuric acid in 1 to 10 mole parts and carboxylic anhydrides such as acetic anhydride and propionic anhydride is added dropwise thereto at −70 to 30° C. for 0.5 to 10 hours, followed by allowing a reaction to take place at −70 to 30° C. for 0.5 to 10 hours with stirring. After completion of the reaction, the reaction solution was poured into ice water at 0 to 30° C., followed by extraction with halogenated hydrocarbons such as methylene chloride, methylene bromide, 1,2-dichloroethane and chloroform, and concentration, to obtain a desired compound shown by the general formula [24]. Then the obtained compound shown by the general formula [24] is dissolved in halogenated hydrocarbons such as methylene chloride, methylene bromide, 1,2-dichloroethane and chloroform, and a solution of a compound ($HA_2$) in an amount of 1 to 10 mole parts relative to 1 mole part of said compound is added thereto, followed by allowing a reaction to take place at 0 to 30° C. for 0.5 to 10 hours with stirring, to obtain an onium salt having a counter anion $A_2$, shown by the general formula [25].

Among the hybrid type onium salts shown by the general formula [1], those having a halogen atom as a counter anion shown by $A_1$ to $A_3$ are useful as a starting material for synthesizing various onium salts of the present invention, while those having a counter anion derived from an inorganic acid shown by the general formula [10] or a compound shown by the general formula [7] (that is onium salts shown by the general formula [34]) are useful as a cationic type photopolymerization initiator, and those having a counter anion derived from an organic acid (that is onium salts shown by the general formula [40]) can also show an excellent effect as an acid generator composing a resist composition used in the production of liquid crystal panels, various semiconductor devices and printed circuit boards. When the onium salt is used as an acid generator composing a resist composition for semiconductor devices, the onium salt having an organic acid as the anion is more preferable.

<1> First, use of the onium salt of the present invention as a cationic type photopolymerization initiator will be explained.

The preferable onium salt of the present invention useful as a cationic type photopolymerization initiator includes, for example, one shown by the general formula [34]:

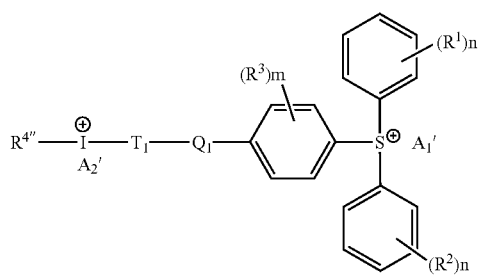

[34]

(wherein $R^1$ to $R^3$, $R^{4''}$, $Q_1$, $T_1$, $A_1{}'$, $A_2{}'$, m and n are the same as described above) (among hybrid type onium salts shown by the general formula [1], corresponding to one wherein a counter anion shown by $A_1$ to $A_3$ is derived from a compound shown by the general formula [7] and an inorganic acid shown by the general formula [10]).

The onium salts of the present invention generate an acid by irradiation with light, whereby polymerization rapidly proceeds if a various kind of α,62 -ethylenically unsaturated monomer, vinyl ether monomer or epoxy monomer exists in the reaction system.

Polymerization or copolymerization of α,β-ethylenically unsaturated monomers, vinyl ether monomers or epoxy monomers, by using the onium salt of the present invention as a polymerization initiator can be performed by a common polymerization reaction of said onium salt and these various monomers in a suitable solvent or without using a solvent under inert gas atmosphere, if necessary.

The α,β-ethylenically unsaturated monomer includes, for example, one shown by the general formula [26]:

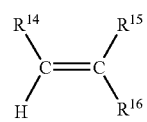

[26]

(wherein $R^{14}$ is a hydrogen atom, a lower alkyl group, a carboxyl group, a carboxyalkyl group, an alkyloxycarbonyl group, a cyano group or an aldehyde group; $R^{15}$ is a hydrogen atom, a lower alkyl group, a carboxyl group, an alkyloxycarbonyl group, a cyano group or a halogen atom; $R^{16}$ is a hydrogen atom, a lower alkyl group, a haloalkyl group, an aryl group which may be substituted, an aliphatic heterocyclic group, an aromatic heterocyclic group, a halogen atom, an alkyloxycarbonyl group, a cyano group, a cyano-containing alkyl group, an acyloxy group, a carboxyl group, a carboxyalkyl group, an aldehyde group, a carbamoyl group or an N-alkylcarbamoyl group; and $R^{14}$ and $R^{15}$ may form an aliphatic ring together with adjacent —C=C— group).

In the general formula [26], the lower alkyl group shown by $R^{14}$ to $R^{16}$ may be straight chained, branched or cyclic, and includes one having generally 1 to 6 carbon atoms, which is specifically exemplified-by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 3-methylpentyl group, a 1,2-dimethylbutyl group, a 2,2-dimethylbutyl group, a 1-ethylbutyl group, a 2-ethylbutyl group, a cyclopropyl group, a cyclobutyl group, a cyclopentyl group and a cyclohexyl group.

In the general formula [26], the carboxyalkyl group shown by $R^{14}$ to $R^{16}$ includes one, wherein a part of hydrogen atoms of the above-described lower alkyl group is substituted by a carboxyl group, which is specifically exemplified by, for example, a carboxymethyl group, a carboxyethyl group, a carboxypropyl group, a carboxybutyl group, a carboxypentyl group and a carboxyhexyl group.

The alkyloxycarbonyl group shown by $R^{14}$ to $R^{16}$ includes one having generally 2 to 11 carbon atoms, which is specifically exemplified by, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a n-heptyloxycarbonyl group, an isoheptyloxycarbonyl group, a sec-heptyloxycarbonyl group, a tert-heptyloxycarbonyl group, a neoheptyloxycarbonyl group, a n-octyloxycarbonyl group, an isooctyloxycarbonyl group, a sec-octyloxycarbonyl group, a tert-octyloxycarbonyl group, a neooctyloxycarbonyl group, a 2-ethylhexyloxycarbonyl group, a n-nonyloxycarbonyl group, an isononyloxycarbonyl group, a sec-nonyloxycarbonyl group, a tert-nonyloxycarbonyl group, a neononyloxycarbonyl group, a n-decyloxycarbonyl group, an isodecyloxycarbonyl group, a sec-decyloxycarbonyl group, a tert-decyloxycarbonyl group and a neodecyloxycarbonyl group.

The halogen atom shown by $R^{15}$ and $R^{16}$ includes, for example, a fluorine atom, a chlorine atom, a bromine atom and an iodine atom.

The haloalkyl group shown by $R^{14}$ to $R^{16}$ includes the above-described lower alkyl group which is halogenated (e.g. fluorinated, chlorinated, brominated and iodinated), and having 1 to 6 carbon atoms, which is specifically exemplified by, for example, a fluoromethyl group, a chloromethyl group, a bromomethyl group, an iodomethyl group, a difluoromethyl group, a dichloromethyl group, a trifluoromethyl group, a trichloromethyl group, a tribromomethyl group, a triiodomethyl group, a fluoroethyl group, a chloroethyl group, a trifluoroethyl group, a trichloroethyl group, a fluoropropyl group, a chloropropyl group, a trifluoropropyl group, a trichloropropyl group, a trifluorobutyl group, a trichlorobutyl group, a trifluoropentyl group, a trichloropentyl group, a trifluorohexyl group and a trichlorohexyl group.

The aryl group of the aryl group which may be substituted, shown by $R^{16}$ includes, for example, a phenyl group, a tolyl group, a xylyl group and a naphthyl group. Said substituent includes, for example, lower alkyl groups having 1 to 4 carbon atoms such as a methyl group, an ethyl group, a n-propyl group, an isopropyl group, a n-butyl group, an isobutyl group, a sec-butyl group and a tert-butyl group; and lower alkoxy groups having 1 to 4 carbon atoms such as a methoxy group, an ethoxy group, a n-propoxy group, an isopropoxy group, a n-butoxy group, an isobutoxy group, a sec-butoxy group and a tert-butoxy group. The specific examples of an aryl group having a substituent includes, for example, a methoxyphenyl group and a tert-butoxyphenyl group.

The aliphatic heterocyclic group shown by $R^{16}$ includes preferably 5- or 6-membered one containing 1 to 3 hetero atoms such as a nitrogen atom, an oxygen atom and a sulfur atom, which is specifically exemplified by, for example, a pyranyl group, an imidazolyl group, a pyrazolyl group, a pyrazinyl group, a pyrimidinyl group, a pyridazinyl group, a pyrrolizinyl group, a pyrrolinyl group, an imidazolinyl group, a pyrazolidinyl group, a pyrazolinyl group, a pipelidinyl group, a piperazinyl group, a morpholinyl group and a quinuclidinyl group.

The aromatic heterocyclic group shown by $R^{16}$ includes preferably 5- or 6-membered one containing 1 to 3 hetero atoms such as a nitrogen atom, an oxygen atom and a sulfur atom, which is specifically exemplified by, for example, a thienyl group, a furyl group, a pyrrolyl group, a pyridyl group, an indolyl group, a purinyl group, a quinolyl group and a carbazolyl group.

The cyano-containing alkyl group shown by $R^{16}$ includes one, wherein a part of hydrogen atoms of the lower alkyl group shown by the above-described $R^{14}$ to $R^{16}$ is substituted by a cyano group, which is specifically exemplified by, for example, a cyanomethyl group, a 2-cyanoethyl group, a 2-cyanopropyl group, a 3-cyanopropyl group, a 2-cyanobutyl group, a 4-cyanobutyl group, a 5-cyanopentyl group and a 6-cyanohexyl group.

The acyloxy group shown by $R^{16}$ includes one derived from a carboxylic acid having generally 2 to 20 carbon atoms, which is specifically exemplified by, for example, an acetyloxy group, a propionyloxy group, a butyryloxy group, an isobutyryloxy group, a valeryloxy group, an isovaleryloxy group, a pivaloyloxy group, a hexanoyloxy group, a heptanoyloxy group, an octanoyloxy group, a nonanoyloxy group, a decanoyloxy group, a dodecanoyloxy group, a tridecanoyloxy group, a tetradecanoyoxy group, a pentadecanoyloxy group, a hexadecanoyloxy group, a heptadecanoyloxy group, an octadecanoyloxy group, a nonadecanoyloxy group, an icosanoyloxy group and a benzoyloxy group.

The N-alkylcarbamoyl group shown by $R^{16}$ includes one, wherein a part of hydrogen atoms of a carbamoyl group is substituted by the above-described lower alkyl group, which is specifically exemplified by, for example, an N-methylcarbamoyl group, an N-ethylcarbamoyl group, an N-n-propylcarbamoyl group, an N-isopropylcarbamoyl group, an N-n-butylcarbamoyl group, an N-isobutylcarbamoyl group, an N-sec-butylcarbamoyl group, an N-tert-butylcarbamoyl group, an N-n-pentylcarbamoyl group, an N-isopentylcarbamoyl group, an N-sec-pentylcarbamoyl group, an N-tert-pentylcarbamoyl group, an N-neopentylcarbamoyl group, an N-n-hexylcarbamoyl group, an N-isohexylcarbamoyl group, an N-sec-hexylcarbamoyl group, an N-tert-hexylcarbamoyl group and an N-neohexylcarbamoyl group.

In the general formula [26], the case where $R^{14}$ and $R^{15}$ forms an aliphatic ring together with the adjacent —C=C— group includes a case where an unsaturated aliphatic ring having 5 to 10 carbon atoms is formed. The ring may be monocyclic or polycyclic. The specific examples of these rings are, for example, a norbornene ring, a cyclopentene ring, a cyclohexene ring, a cyclooctene ring and a cyclodecene ring.

The vinyl ether monomer includes one shown by the general formula [27];

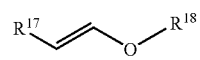

[27]

[wherein $R^{17}$ is a hydrogen atom or a lower alkyl group; $R^{18}$ is an alkyl group, a group shown by the formula [28]

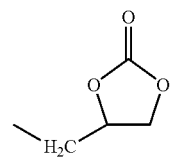

[28]

or a group shown by the formula [29]:

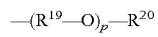

[29]

(wherein $R^{19}$ is an alkylene group; $R^{20}$ is a hydrogen atom or a vinyl group; and p is an integer of 1 to 3)].

In the general formula [27], the lower alkyl group shown by $R^{17}$ includes the same as examples of a lower alkyl group shown by $R^{14}$ to $R^{16}$ in the general formula [26].

The alkyl group shown by $R^{18}$ may be straight chained, branched or cyclic, and includes one having generally 1 to 15 carbon atoms, preferably 1 to 12 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a cyclopropyl group, a cyclobutyl group, a cyclopentyl group, cyclohexyl group, a cycloheptyl group, a cyclooctyl group, a cyclononyl group and a cyclodecyl group.

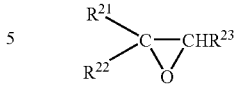

[30]

[wherein $R^{21}$ and $R^{22}$ are each independently a hydrogen atom, a lower alkyl group, an aryl group or a carboxyl group; $R^{23}$ is a hydrogen atom, an alkyl group, a lower haloalkyl group, a lower hydroxyalkyl group, an aryl group, a lower alkoxycarbonyl group, a carboxyl group, a group shown by the general formula [31];

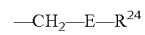

[31]

(wherein E is an oxygen atom or —OCO— group; and $R^{24}$ is an alkyl group, a lower alkenyl group or an aryl group), an epoxyethyl group or an epoxycyclohexyl group; and $R^{21}$ and $R^{22}$ may form an aliphatic ring together with the adjacent carbon atoms], or one shown by the general formula [32];

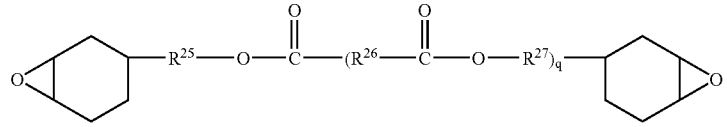

[32]

In the general formula [29], the alkylene group shown by $R^{19}$ may be straight chained, branched or cyclic, and includes one having generally 2 to 10 carbon atoms, preferably 2 to 8 carbon atoms, which is specifically exemplified by, for example, linear alkylene groups such as a methylene group, an ethylene group, a trimethylene group, a tetramethylene group, a pentamethylene group, a hexamethylene group, a heptamethylene group, an octamethylene group, a nonamethylene group and a decamethylene group; branched alkylene groups such as an ethylidene group, a propylene group, an isopropylidene group, a 1-methyltrimethylene group, a 2-methyltrimethylene group, a 1,1-dimethylethylene group, a 1,2-dimethylethylene group, an ethylethylene group, a 1-methyltetramethylene group, a 1,1-dimethyltrimethylene group, a 2,2-dimethyltrimethylene group, a 2-ethyltrimethylene group, a 1-methylpentamethylene group, a 2-methylpentamethylene group, a 1,3-dimethyltetramethylene group, a 3-ethyltetramethylene group, a 1-methylhexamethylene group, a 1-methylheptamethylene group, a 1,4-diethyltetramethylene group, a 2,4-dimethylheptamethylene group, a 1-methyloctamethylene group and a 1-methylnonamethylene group; and cyclic alkylene groups such as a cyclopropylene group, a 1,3-cyclobutylene group, a 1,3-cyclopentylene group, a 1,4-cyclohexylene group, a 1,5-cycloheptylene group, a 1,5-cyclooctylene group, a 1,5-cyclononylene group and a 1,6-cyclodecylene group.

The epoxy monomer includes one shown by the general formula [30]:

(wherein $R^{25}$ to $R^{27}$ are each independently a lower alkylene chain; and q is an integer of 0 or 1) and the like.

In the general formulae [30] and [31], the lower alkyl group shown by $R^{21}$ and $R^{22}$ may be straight chained, branched or cyclic, and includes one having generally 1 to 6 carbon atoms, preferably 1 to 3 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group; a neopentyl group, a n-hexyl group, an isohexyl group, a sec-hexyl group, a tert-hexyl group, a neohexyl group, a cyclopropyl group, a cyclobutyl group, a cyclopentyl group and a cyclohexyl group.

The aryl group shown by $R^{21}$ to $R^{24}$ includes one having generally 6 to 15 carbon atoms, preferably 6 to 10 carbon atoms, which is specifically exemplified by, for example, a phenyl group, a naphthyl group, an anthryl group and phenanthryl group.

The alkyl group shown by $R^{23}$ and $R^{24}$ maybe straight chained, branched or cyclic, and includes one having generally 1 to 18 carbon atoms, preferably 1 to 16 carbon atoms, which is specifically exemplified by, for example, the same as examples of the lower alkyl group shown by $R^{21}$ and $R^{22}$, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a cycloheptyl group, a cyclooctyl group, a cyclononyl group and a cylodecyl group.

In the general formula [30], the lower haloalkyl group shown by $R^{23}$ includes the above-described lower alkyl group shown by $R^{21}$ and $R^{22}$, halogenated (e.g. fluorinated, chlorinated, brominated and iodinated), and having generally 1 to 6 carbon atoms, preferably 1 to 3 carbon atoms, which is specifically exemplified by, for example, a fluoromethyl group, a chloromethyl group, a bromomethyl group, an iodomethyl group, a difluoromethyl group, a dichloromethyl group, a trifluoromethyl group, a trichloromethyl group, a tribromomethyl group, a triiodomethyl group, a pentafluoroethyl group, a pentachloroethyl group, a pentabromoethyl group, a pentaiodoethyl group, a heptafluoropropyl group, a heptachloropropyl group, a heptabromopropyl group, a heptaiodopropyl group, a nonafluorobutyl group, a nonachlorobutyl group, a nonabromobutyl group, a nonaiodobutyl group, a perfluoropentyl group, a perchloropentyl group, a perfluorohexyl group and a perchlorohexyl group.

The lower hydroxyalkyl group shown by $R^{23}$ includes, for example, one, wherein terminal hydrogen atom of the lower alkyl group shown by the above-described $R^{21}$ and $R^{22}$ is substituted by a hydroxyl group.

The lower alkoxycarbonyl group shown by $R^{23}$ maybe straight chained, branched or cyclic, and includes one having generally 2 to 7 carbon atoms, preferably 2 to 4 carbon atoms, which is specifically exemplified by, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a cyclopropyloxycarbonyl group, a cyclobutyloxycarbonyl group, a cyclopentyloxycarbonyl group and a cyclohexyloxycarbonyl group.

In the general formula [31], the lower alkenyl group shown by $R^{24}$ may be straight chained, branched or cyclic, and includes one having generally 2 to 6 carbon atoms, preferably 2 to 3 carbon atoms, which is specifically exemplified by, for example, a vinyl group, an allyl group, a 1-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, a 2-methyl-2-butenyl group, a 1-hexenyl group, a 2-hexenyl group, a 3-hexenyl group, a 5-hexenyl group, a 2-methyl-2-pentenyl group, a 1-cyclobutenyl group, 1-cyclopentenyl group and a 1-cyclohexenyl group.

In the general formula [30], the case where $R^{21}$ and $R^{23}$ forms an aliphatic ring together with the adjacent carbon atoms includes a case where a saturated aliphatic ring having 5 to 10 carbon atoms is formed. The specific examples of these rings are, for example, a cyclopentane ring, a cyclohexane ring, a cycloheptane ring, a cyclooctane ring, a cyclononane ring and a cyclodecane ring. These aliphatic rings may further be condensed with an aromatic ring such as a benzene ring or a naphthalene ring.

In the general formula [32], the lower alkylene chain shown by $R^{25}$ to $R^{27}$ includes one having generally 1 to 6 carbon atoms, preferably 1 to 4 carbon atoms, which is specifically exemplified by, for example, a methylene group, an ethylene group, a trimethylene group, a tetramethylene group, a pentamethylene group and a hexamethylene group.

The specific examples of the α,β-ethylenically unsaturated monomer shown by the general formula [26] are, for example, ethylenically unsaturated aliphatic hydrocarbons having 2 to 20 carbon atoms such as ethylene, propylene, butylene and isobutylene; ethylenically unsaturated aromatic hydrocarbons having 8 to 20 carbon atoms such as styrene, 4-methylstyrene and divinylbenzene; alkenyl esters having 3 to 20 carbon atoms such as vinyl formate, vinyl acetate, vinyl propionate and isopropenyl acetate; halogen-containing ethylenically unsaturated compounds having 2 to 20 carbon atoms such as vinyl chloride, vinylidene chloride, vinylidene fluoride and tetrafluoroethylene; ethylenically unsaturated carboxylic acids having 3 to 20 carbon atoms such as acrylic acid, methacrylic acid, itaconic acid, maleic acid, fumaric acid, crotonic acid, vinylacetic acid, allylacetic acid and vinylbenzoic acid (these acids may form an alkaline metal salt such as sodium salt and potassium salt or ammonium salt); ethylenically unsaturated carboxylate esters such as methyl methacrylate, ethyl methacrylate, propyl methacrylate, butyl methacrylate, 2-ethylhexyl methacrylate, methyl acrylate, ethyl acrylate, propyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenoate; cyano-containing ethylenically unsaturated compounds having 3 to 20 carbon atoms such as acrylonitrile, methacrylonitrile and allyl cyanide; ethylenically unsaturated amide compounds having 3 to 20 carbon atoms such as acrylamide and methacrylamide; ethylenically unsaturated aldehydes having 3 to 20 carbon atoms such as acrolein and croton aldehyde; ethylenically unsaturated aliphatic heterocyclic amines having 5 to 20 carbon atoms such as N-vinylpyrrolidone and vinylpiperidine; and ethylenically unsaturated aromatic heterocyclic amines having 5 to 20 carbon atoms such as vinylpyridine and 1-vinylimidazole.

The specific examples of the vinyl ether monomer shown by the general formula [27] are, for example, alkyl vinyl ethers such as methyl vinyl ether, ethyl vinyl ether, propyl vinyl ether, isobutyl vinyl ether, 2-ethylhexy vinyl ether, octadecyl vinyl ether, dodecyl vinyl ether and cyclohexyl vinyl ether; hydroxyalkyl vinyl ethers such as hydroxyethyl vinyl ether, hydroxybutyl vinyl ether, di(ethyleneglycol) monovinyl ether and 1,4-cyclohexanedimethanol monovinyl ether; divinyl ethers such as 1,4-butanediol divinylether, 1,6-hexanediol divinylether, 1,4-cyclohexanedimethanol divinylether, di(ethyleneglycol) divinylether, tri(ethyleneglycol) divinylether, di(propyleneglycol) divinylether and tri(propyleneglycol) divinylether, and propylene carbonate propenyl ether.

The specific examples of the epoxy monomer shown by the general formula [30] are, for example, epoxyalkanes such as ethylene oxide, 1,2-epoxypropane, 1,2-epoxybutane, 2,3-epoxybutane, 1,2-epoxypentane, 2,3-epoxypentane, 1,2-epoxyhexane, 1,2-epoxyheptane, 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxyhexadecane, 1,2-epoxyheptadecane, and 1,2-epoxyoctadecane; epoxyhaloalkanes such as 2,3-epoxy-1,1,1-trifluoropropane, and 2,3-epoxy-1-chloropropane; epoxyalcohols such as 2,3-epoxypropanol; alkyl glycidyl ethers such as methyl glycidyl ether, ethyl glycidyl ether, propyl glycidyl ether, butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, and dodecyl glycidyl ether; aryl glycidyl ethers such as phenyl glycidyl ether and naphthyl glycidyl ether; alkenyl glycidyl ethers such as allyl glycidyl ether; glycidyl esters such as glycidyl methacrylate; 2,3-epoxyethylbenzene, α, α'-epoxybibenzyl, 2,3-epoxy-2,3-dihydro-1,4-naphthoquinone, epoxysuccinic acid, ethyl 2,3-epoxy-3-phenylbutyrate, 1,2,3,4-diepoxybutane, and 1,2-epoxy-5-(epoxyethyl)cyclohexane.

The specific examples of the epoxy monomer shown by the general formula [32] are, for example, bis(3,4-epoxycyclohexyl)adipate and 3,4-epoxycyclohexyl-3,4-epoxycyclohexanecarboxylic acid.

These monomers may be used alone or in a suitable combination of two or more kinds thereof.

The above-described polymerization method includes, for example, a solution polymerization, a bulk polymerization, a suspension polymerization and an emulsion polymerization.

The solvent for polymerization includes, for example, halogenated hydrocarbons such as chloroform, methylene chloride and 1,2-dichloroethane; hydrocarbons such as toluene, benzene and xylene; N,N-dimethylformamide and dimethylsulfoxide.

These solvents may be used alone or in a suitable combination of two or more kinds thereof.

The polymerization is desirably performed under an inert gas atmosphere. The inert gas includes, for example, nitrogen gas and argon gas.

An amount of the onium salt compound of the present invention to be used depends on kinds of an α,β-ethylenically unsaturated monomer, a vinyl ether monomer or an epoxy monomer, and generally 0.1 to 200 wt %, preferably 1 to 50 wt % relative to various monomers.

A concentration of the α,β-ethylenically unsaturated monomer, a vinyl ether monomer or an epoxy monomer in the polymerization depends on kinds of various monomers, and generally 1 to 100 wt % (no solvent), preferably 10 to 80 wt %. A polymerization temperature is generally −78 to 120° C., preferably −20 to 50° C.

A polymerization time depends on reaction conditions such as a reaction temperature, kinds of an onium salt compound of the present invention and various monomers to be reacted or concentrations thereof and the like, and generally 1 to 50 hours.

Post-treatment after the reaction may be performed in accordance with common methods generally performed in this field.

<2> Secondly, use of the onium salt of the present invention as an acid generator for a chemically amplified resist composition will be explained.

The preferable onium salt of the present invention used as an acid generator includes one shown by the general formula [40];

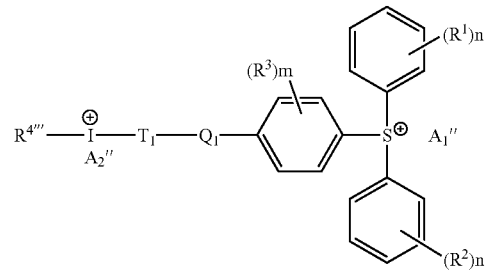

(wherein $R^1$ to $R^3$, $R^{4\prime\prime\prime}$, $Q_1$, $T_1$, $A_1''$, $A_2''$, m and n are the same as described above), (among hybrid type onium salts shown by the general formula [1], corresponding to one wherein a counter anion shown by $A_1$ to $A_3$ is derived from a compound shown by the general formula [7], an organic acid or an inorganic acid).

The onium salts of the present invention shown by the general formula [40] can be used alone as an acid generator, and more excellent effect can be expected by use of the salt in a combination with other acid generators. In particular, the onium salt of the present invention shows a remarkably excellent effect as an acid generator when the salt is used in combination with an acid generator generating a weak acid such as diazodisulfone compound having an alkyl group as a pending group.

The diazodisulfone compound used in combination includes, for example, one shown by the general formula [33];

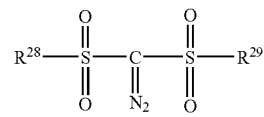

(wherein $R^{28}$ and $R^{29}$ are each independently an alkyl group).

In the general formula [33], the alkyl group shown by $R^{28}$ may be straight chained, branched or cyclic, and includes one having generally 1 to 8 carbon atoms, preferably 3 to 8 carbon atoms, and among others, preferably branched or cyclic one, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a 3-methylpentyl group, a 2-methylpentyl group, a 1,2-dimethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a cyclopropyl group, a cyclobutyl group, a cyclopentyl group, a cyclohexyl group, a cycloheptyl group and a cyclooctyl group.

The alkyl group shown by $R^{29}$ may be straight chained, branched or cyclic, and includes one having generally 3 to 8 carbon atoms, and among others, preferably branched or cyclic one, which is specifically exemplified by, for example, an isopropyl group, an isobutyl group, a sec-butyl group, a tert-butyl group, an isopentyl group, a sec-pentyl group, a tert-pentyl group, a neopentyl group, an isohexyl group, a sec-hexyl group, a tert-hexyl group, a neohexyl group, a 3-methylpentyl group, a 2-methylpentyl group, a 1,2-dimethylbutyl group, an isoheptyl group, a sec-heptyl group, a tert-heptyl group, a neoheptyl group, an isooctyl group, a sec-octyl group, a tert-octyl group, a neooctyl group, a cyclopropyl group, a cyclobutyl group, a cyclopentyl group, a cyclohexyl group, a cycloheptyl group and a cyclooctyl group.

The specific examples of the diazodisulfone compound shown by the general formula [33] are, for example, bis(1-methylethylsulfonyl)diazomethane, bis(1,1-dimethylethylsulfonyl)diazomethane, bis(cyclohexylsulfonyl)diazomethane, methylsulfonyl-1-methylethylsulfonyldiazomethane, methylsulfonyl-1,1-dimethylethylsulfonyldiazomethane, ethylsulfonylcyclohexylsulfonyldiazomethane, ethylsulfonyl-1-methylethylsulfonyldiazomethane, ethylsulfonyl-1,1-dimethylethylsulfonyldiazomethane, ethylsulfonylcyclohexylsulfonyldiazomethane, bis(octylsulfonyl)diazomethane, methylethylsulfonyl-1,1-dimethylethylsulfonyldiazomethane, 1-methylethylsulfonylcyclohexylsulfonyldiazomethane and 1,1-dimethylethylsulfonylcyclohexylsulfonyldiazomethane.

An amount of the onium salt shown by the general formula [40] of the present invention to be used is, when used alone, generally 0.1 to 10 wt %, preferably 0.5 to 5 wt %, relative to the resin amount of a chemically amplified resist composition, and when used together with other kind of acid generator, generally 0.05 to 5 wt %, preferably 0.1 to 3 wt %, relative to the resin amount, while an amount of the other kind of acid generator is generally 1 to 10 wt %, preferably 3 to 7 wt %, relative to the resin amount.

The onium salt of the present invention shown by the general formula [40], can generate an acid by irradiation with deep UV, KrF excimer laser, i-line, ArF excimer laser, $F_2$ laser (157 nm), electron beams, soft X-rays or the like. Therefore, the sulfonium salt of the present invention shown by the general formula [40] is useful as an acid generator for a chemically amplified type resist by irradiation with deep UV, KrF excimer laser, i-line, ArF excimer laser, $F_2$ excimer laser (157 nm), electron beams (EB) and soft X-rays, in particular, KrF excimer laser, ArF excimer laser, $F_2$ excimer laser (157 nm) or electron beams (EB).

Since the onium salt of the present invention shown by the general formula [40] has a plurality of counter anions in the molecule, it has an improved acid generation efficiency by irradiation with, for example, UV, deep V, KrF excimer laser, ArF excimer laser, $F_2$ excimer laser, electron beams or X-rays. Therefore, when the onium salt is used as a cationic type photopolymerization initiator, it can form a polymer with high hardness, and when the onium salt is used as an acid generator for a resist, it can provide a resist composition with high sensitivity due to improved solubility in a solvent for a resist with low polarity such as PGMEA or ethyl lactate.

A conventional sulfonium salt or iodonium salt, including as a counter anion $PF_6^-$, $BF_4^-$ and the like, has a problem that photocuring is significantly lowered. However, the onium salt of the present:invention shown by the general formula [40] can also form a polymer with high hardness without having such problem, even when these counter anions are used.

Further, the onium salt of the present invention shown by the general formula [40] is a hybrid type compound having a sulfonium salt and an iodonium salt in the molecule, and therefore, can be efficiently dissolved in monomers or oligomers without having a problem of low solubility in monomers or oligomers, which is observed in case of use of known triaryl type sulfonium salt or a diaryl type iodonium salt.

In the following, the present invention is explained in detail referring to examples, but the present invention is not limited thereto by any means.

EXAMPLE

Example 1

Synthesis of 4-[4-(diphenylsulfonio)phenylthio]phenyl-phenyl iodonium bis(hexafluorophosphate), (corresponding to the compound shown by the general formula [4])

(1) Synthesis of diphenyl-4-phenylthiophenylsulfonium trifluoromethanesulfonate

In 400 ml of dichloromethane were dissolved 40.4 g (0.2 mol) of diphenylsulfoxide and 37.2 g (0.2 mol) of diphenylsulfide, and 50.4 g (0.24 mol) of trifluoroacetic anhydride was added thereto at 0° C. Then 30.0 g (0.2 mol) of trifluoromethanesulfonic acid was added dropwise to the resultant at 0 to 5° C., followed by gradually warming to room temperature and reacting for 2 hours with stirring. After completion of the reaction, the reaction solution was washed with 400 ml of water five times and concentrated under reduced pressure, followed by purifying the resulting crude product by a column chromatography to obtain 33.2 g (Yield: 32%) of diphenyl-4-phenylthiophenylsulfonium trifluoromethanesulfonate as a yellow oily substance.

$^1$HNMR (CDCl$_3$) δ Pam: 7.27–7.29 (2H, m, Ar—H), 7.44–7.47 (3H, m, Ar—H), 7.52–7.57 (4H, m, Ar—H), 7.67–7.75 (10H, m, Ar—H)

(2) Synthesis of 4-[4-(diphenylsulfonio)phenylthio]phenyl-phenyl iodonium bis(hexafluorophosphate)

In 30 ml of acetic anhydride was dissolved 5.2 g (0.01 mol) of diphenyl-4-phenylthiophenylsulfonium trifluoromethanesulfonate obtained in the above-described (1), and 3.2 g (0.01 mol) of iodobenzene diacetate was added thereto at 0° C. Then 4.6 g (0.04 mol) of trifluoroacetic acid was added dropwise at 0 to 4° C. for 30 minutes, followed by gradually warming to room temperature and reacting for 2 hours with stirring. After completion of the reaction, the reaction solution was poured into 200 ml of ice water and 7.4 g (0.04 mol) of potassium hexafluorophosphate was added thereto, followed by adding 200 ml of dichloromethane and stirring for 2 hours at room temperature. Then, the solution was fractionated, and 200 ml of water was poured into the resulting dichloromethane layer, and then sodium hydrocarbonate was added thereto until the solution became neutral, followed by fractionating again. The obtained dichloromethane layer was washed with 200 ml of water and concentrated and evaporated to dryness under reduced pressure, followed by purifying the resulting crude product by a column chromatography to obtain 6.6 g (Yield: 69%) of 4-[4-(diphenylsulfonio)phenylthio]phenyl-phenyl iodonium bis(hexafluorophosphate) as a pale yellow glassy substance.

¹HNMR (CDCl₃) δ ppm: 7.09–7.49 (4H, m, Ar—H), 7.65–7.77 (17H, m, Ar—H), 7.94 (2H, d, Ar—H) IR (cm⁻¹) : 4065, 3661, 3065, 1572, 1476, 1447, 1391, 1291, 1184, 1051, 1009, 845, 750, 689, 608, 569, 515, 407

Example 2

Synthesis of bis{4-[4-(diphenylsulfonio)phenylthio]phenyl}iodonium tris(hexafluorophosphate) (corresponding to the compound shown by the general formula [11])

In 20 ml of acetic anhydride was dissolved 5.2 g (0.01 mol) of diphenyl-4-phenylthiophenylsulfonium trifluoromethanesulfonate obtained in Example 1, and 1.07 g (0.005 mol) of potassium iodate was added thereto at 0° C. Then a mixed acid consisted of 2.5 g (0.025 mol) of concentrated sulfuric acid and 3.0 g of acetic anhydride was added dropwise thereto at 0 to 3° C. for 1 hour, followed by gradually warming to room temperature and reacting for 9 hours with stirring. After completion of the reaction, the reaction solution was poured into 200 ml of ice water and 5.55 g (0.03 mol) of potassium hexafluorophosphate was added thereto, followed by adding 200 ml of dichloromethane thereto and stirring for 2 hours at room temperature. Then, the solution was fractionated, and 200 ml of water was poured into the resulting dichloromethane layer, and then sodium hydrocarbonate was added thereto until the solution became neutral, followed by fractionating again. The obtained dichloromethane layer was washed with 200 ml of water and concentrated and evaporated to dryness under reduced pressure, followed by purifying the resulting crude product by a column chromatography to obtain 2.83 g (Yield: 44%) of bis{4-[4-(diphenylsulfonio)phenylthio]phenyl}iodonium tris(hexafluorophosphate) as a pale yellow glassy substance.

¹HNMR (CDCl₃) δ ppm: 7.24–7.32 (6H, m, Ar—H), 7.43–7.54 (9H, m, Ar—H), 7.62–7.77 (21H, m, Ar—H) IR (cm⁻¹): 3094, 1572, 1475, 1447, 1397, 1186, 1067, 1003, 945, 750, 685, 563, 544, 494, 467, 417

Example 3

Synthesis of bis{4-[4-(diphenylsulfonio)phenoxy]phenyl}iodonium tris(hexafluorophosphate) (corresponding to the compound shown by the general formula [12])

(1) Synthesis of diphenyl-4-phenoxyphenylsulfonium trifluoromethanesulfonate

In 100 ml of dichloromethane were dissolved 10.1 g (0.05 mol) of diphenylsulfoxide and 8.51 g (0.05 mol) of diphenyl ether, and 12.6 g (0.06 mol) of trifluoroacetic anhydride was added thereto at 0° C. Then 7.5 g (0.05 mol) of trifluoromethanesulfonic acid was added dropwise thereto at 0 to 5° C., followed by gradually warming to room temperature and reacting for 2 hours with stirring. After completion of the reaction, the reaction solution was washed with 100 ml of water five times and concentrated under reduced pressure, followed by purifying the resulting crude product by a column chromatography to obtain 9.59 g (Yield: 38%) of diphenyl-4-phenoxyphenylsulfonium trifluoromethanesulfonate as a yellow oily substance.

¹HNMR (CDCl₃) δ ppm: 7.09 (2H, d, Ar—H), 7.19 (2H, m, Ar—H), 7.27 (1H, t, Ar—H), 7.42 (2H, t, Ar—H), 7.70–7.77 (12H, m, Ar—H)

(2) Synthesis of bis{4-[4-(diphenylsulfonio)phenoxy]phenyl}iodonium tris(hexafluorophosphate)

The same procedure as in Example 2 was conducted except for using 5.04 g (0.01 mol) of diphenyl-4-phenoxyphenylsulfonium trifluoromethanesulfonate obtained by the above-described (1), to obtain 3.69 g (Yield: 58%) of bis{4-[4-(diphenylsulfonio)phenoxy]phenyl}iodonium tris(hexafluorophosphate) as a pale brown glassy substance.

¹HNMR (CDCl₃) δ ppm: 7.18 (4H, d, Ar—H), 7.30 (4H, d, Ar—H), 7.67–7.83 (24H, m, Ar—H), 8.08 (4H, d, Ar—H) IR (cm⁻¹) : 3675, 1568, 1478, 1449, 1250, 1175, 997, 839, 750, 685, 567, 532, 517, 496, 478, 459, 436

Example 4

Synthesis of bis[4-(diphenylsulfonio)(1,1'-biphenyl)-4'-yl]iodonium tris(hexafluorophosphate) (corresponding to the compound shown by the general formula [13])

(1) Synthesis of 4-biphenylyl-diphenylsulfonium trifluoromethanesulfonate

In 35 ml of n-hexane were suspended 6.07 g (0.03 mol) of diphenylsulfoxide and 5.55 g (0.036 mol) of biphenyl, and 7.56 g (0.036 mol) of trifluoroacetic anhydride was poured thereinto at 0° C. Then 4.5 g (0.03 mol) of trifluoromethanesulfonic acid as added dropwise thereto at 0 to 5° C., followed by gradually warming to room temperature and reacting for 4 hours with stirring. After completion of the reaction, 50 ml of water was poured into the reaction solution and the n-hexane layer was removed by fractionation. The aqueous layer was further washed with 50 ml of n-hexane three times and extracted with 60 ml of dichloromethane. The resulting dichloromethane layer was washed with 50 ml of water five times, followed by concentration under reduced pressure to obtain 14.5 g (Yield: 99%) of 4-biphenylyl-diphenylsulfonium trifluoromethanesulfonate as a brown oily substance.

¹HNMR (CDCl₃) δ ppm: 7.42–7.50 (3H, m, Ar—H), 7.56–7.60 (2H, d, Ar—H), 7.67–7.78 (10H, m, Ar—H), 7.81 (2H, dd, Ar—H), 7.88 (2H, dd, Ar—H)

(2) Synthesis of bis[4-(diphenylsulfonio)(1,1'-biphenyl)-4'-yl]iodonium tris(hexafluorophosphate)

The same procedure as in Example 2 was conducted except for using 4.89 g (0.01 mol) of 4-biphenylyl-diphenylsulfonium trifluoromethanesulfonate obtained by the above-described (1), to obtain 3.78 g (Yield: 61%) of bis[4-(diphenylsulfonio)(1,1'-biphenyl)-4'-yl]iodonium tris(hexafluorophosphate) as a pale brown glassy substance.

¹HNMR (CDCl₃) δ ppm: 7.31–7.47 (2H, dd, Ar—H), 7.57–7.59 (2H, dd, Ar—H), 7.64–7.78 (28H, m, Ar—H), 7.84–7.89 (4H, m, Ar—H) IR (cm⁻¹): 1590, 1478, 1449, 1069, 999, 843, 750, 683, 565, 529, 515, 492, 469, 449, 424

Example 5

Synthesis of bis{4-[4-(diphenylsulfonio)phenylmethyl]phenyl}iodonium tris(hexafluorophosphate) (corresponding to the compound shown by the general formula [14])

(1) Synthesis of Diphenyl-4-phenylmethylphenylsulfonium trifluoromethanesulfonate In 35 ml of n-hexane were suspended 6.07 g (0.03 mol) of diphenylsulfoxide and 6.06 g (0.036 mol) of diphenylmethane, and 7.56 g (0.036 mol) of trifluoroacetic anhydride was added thereto at 0° C. Then 4.5 g (0.03 mol) of trifluoromethanesulfonic acid was added dropwise thereto at 0 to 5° C., followed by gradually warming to room temperature and reacting for 4 hours with stirring. After completion of the reaction, 50 ml of water was poured into the reaction solution and the n-hexane layer was removed by fractionation. The aqueous layer was further washed with 50 ml of hexane three times and extracted with 60 ml of dichloromethane. The resulting dichloromethane layer was washed with 50 ml of water five times, followed by concentration under reduced pressure. 70 ml of ethyl acetate was poured into the resulting crude crystal, followed by dissolving by warming to 60° C., cooling to room temperature, the resulting crude crystal was filtered and dried under vacuum to obtain 11.3 g (Yield: 75%) of diphenyl-4-phenylmethylphenylsulfonium trifluoromethanesulfonate as a pale brown crystal.

Melting point: 125–129° C. $^1$HNMR (CDCl$_3$) δ ppm: 4.05 (2H, s, CH), 7.14–7.16 (2H, m, Ar—H), 7.22–7.29 (3H, m, Ar—H), 7.47 (2H, d, Ar—H), 7.61–7.72 (12H, m, Ar—H)

(2) Synthesis of bis{4[4-(diphenylsulfonio)phenylmethyl]phenyl}iodonium tris(hexafluorophosphate)

The same procedure as in Example 2 was conducted except for using 5.03 g (0.01 mol) of diphenyl-4-phenylmethylphenylsulfonium trifluoromethanesulfonate obtained, to obtain 1.75 g (Yield: 28%) of bis{4[4-(diphenylsulfonio)phenylmethyl]phenyl}iodonium tris(hexafluorophosphate) as a white glassy substance.

$^1$HNMR (CDCl$_3$) δ ppm: 4.14 (4H, s, CH$_2$), 7.42 (4H, d, Ar—H), 7.63 (4H, d, Ar—H), 7.74–7.80 (20H, m, Ar—H), 7.83–7.87 (4H, m, Ar—H), 8.14 (4H, d, Ar—H) IR (cm$^{-1}$): 3675, 3100, 1580, 1478, 1449, 1406, 1188, 1069, 997, 845, 750, 685, 563, 532, 511, 498, 457, 434, 409

Example 6

Synthesis of bis{4[4-(diphenylsulfonio)phenylthio]phenyl}iodonium tris(trifluoromethanesulfonate) (corresponding to the compound shown by the general formula [11])

The same procedure as in Example 2 was conducted except for using 4.5 g (0.03 mol) of trifluoromethanesulfonate instead of 5.55 g (0.03 mol) of potassium hexafluorophosphate used in Example 2, to obtain 3.3 g (Yield: 50%) of bis{4[4-(diphenylsulfonio)phenylthio]phenyl}iodonium tris(trifluoromethanesulfonate) as a yellow brown oily substance.

$^1$HNMR (CDCl$_3$) δ ppm: 7.23–7.32 (6H, m, Ar—H), 7.44–7.46 (2H, m, Ar—H), 7.52–7.60 (6H, m, Ar—H), 7.67–7.78 (22H, m, Ar—H) IR (cm$^{-1}$): 3501, 3063, 1572, 1476, 1447, 1397, 1271, 1157, 1067, 1030, 1003, 818, 752, 685, 637

Example 7

Synthesis of bis{4[4-(diphenylsulfonio)phenylthio]phenyl}iodonium tris(nonafluorobutanesulfonate) (corresponding to the compound shown by the general formula [11])

(1) Synthesis of diphenyl-4-phenylthiophenylsulfonium nonafluorobutanesulfonate

In 50 ml of dichloromethane were dissolved 6.07 g (0.03 mol) of diphenylsulfoxide and 11.2 g (0.06 mol) of diphenylsulfide, and 7.56 g (0.036 mol) of trifluoroacetic anhydride was poured thereinto at 0° C. Then 9.0 g (0.03 mol) of nonafluorobutanesulfonic acid was added dropwise at 0 to 5° C., followed by gradually warming to room temperature and reacting for 2 hours with stirring. After completion of the reaction, the reaction solution was washed with 100 ml of water five times and concentrated under reduced pressure, followed by purifying the resulting crude product by a column chromatography to obtain 7.85 g (Yield: 39%) of diphenyl-4-phenylthiophenylsulfonium nonafluorobutanesulfonate as a yellow oily substance.

$^1$HNMR (CDCl$_3$) δ ppm: 7.25–7.28 (2H, m, Ar—H), 7.43–7.47 (3H, m, Ar—H), 7.52–7.57 (4H, m, Ar—H), 7.65–7.75 (10OH, m, Ar—H)

(2) Synthesis of bis{4[4-(diphenylsulfonio)phenylthio]phenyl}iodonium tris(nonafluorobutanesulfonate)

In 20 ml of acetic anhydride was dissolved 6.71 g (0.01 mol) of diphenyl-4-phenylthiophenylsulfonium nonafluorobutanesulfonate obtained in the above-described (1), and 1.07 g (0.005 mol) of potassium iodate was added thereto at 0° C. Then a mixed acid consisted of 2.5 g (0.025 mol) of concentrated sulfuric acid and 3.0 g of acetic anhydride was added dropwise at 0 to 3° C. for 1 hour, followed by gradually warming to room temperature and reacting for 9 hours with stirring. After completion of the reaction, the reaction solution was poured into 200 ml of ice water and 9.0 g (0.03 mol) of nonafluorobutanesulfonic acid was added thereto, followed by adding 200 ml of dichloromethane and stirring at room temperature for 2 hours. Then, the solution was fractionated, and 200 ml of water was poured into the resulting dichloromethane layer, then with sodium hydrocarbonate was added thereto until the solution became neutral, followed by fractionating again. The resulting dichloromethane layer was washed with 200 ml of water and concentrated to dryness under reduced pressure, followed by purifying the resulting crude product by a column chromatography to obtain 3.88 g (Yield: 44%) of bis{4[4-(diphenylsulfonio)phenylthio]phenyl}iodonium tris(nonafluorobutanesulfonate).

$^1$HNMR (CDCl$_3$) δ ppm: 7.23–7.32 (6H, m, Ar—H), 7.43–7.44 (2H, m, Ar—H), 7.45–7.60 (6H, m, Ar—H), 7.62–7.78 (22H, m, Ar—H) IR (cm$^{-1}$): 3499, 3065, 1572, 1476, 1447, 1397, 1353, 1267, 1055, 1005, 870, 816, 748, 685, 654

Example 8

Synthesis of bis{4-[4-(diphenylsulfonio)phenylthio]phenyl}iodonium tris(pentafluorobenzenesulfonate) (corresponding to the compound shown by the general formula [11])

(1) Synthesis of dipheny-4-phenylthiophenylsulfonium bromide

In 200 ml of n-hexane were suspended 6.07 g (0.03 mol) of diphenylsulfoxide and 11.2 g (0.06 mol) of diphenylsulfide, and 48.0 g (0.18 mol) of aluminum bromide was added thereto at 20 to 40° C., followed by reacting at 60 to 65° C. for 6 hours with stirring. After completion of the reaction, the reaction solution was poured into 500 ml of 12% hydrobromic acid, followed by washing with 200 ml of n-hexane five times and extracting with 200 ml of dichloromethane. The obtained dichloromethane layer was washed with 200 ml of water five times, followed by concentration under reduced pressure to obtain a crude product. Then, 120 ml of acetone was added to the crude product to dissolve at 55° C., followed by cooling to 5° C. to obtain crystal. The crystal was filtered off to obtain 5.3 g (Yield: 39%) of dipheny-4-phenylthiophenylsulfonium bromide as a pale yellow crystal.

Melting point: 129–131° C. $^1$HNMR (CDCl$_3$) δ ppm: 7.26–7.28 (2H, m, Ar—H), 7.45–7.47 (3H, m, Ar—H), 7.53–7.54 (2H, m, Ar—H), 7.64–7.75 (8H, m, Ar—H), 7.83–7.84 (4H, m, Ar—H)

(2) Synthesis of bis{4-[4-(diphenylsulfonio)phenylthio]phenyl}iodonium tris(pentafluorobenzenesulfonate)

In 20 ml of acetic anhydride was dissolved 4.51 g (0.01 mol) of dipheny-4-phenylthiophenyllsulfonium bromide obtained in the above-described (1), and 1.07 g (0.005 mol) of potassium iodate was added thereto at 0° C. Then a mixed acid consisted of 2.5 g (0.025 mol) of concentrated sulfuric acid and 3.0 g of acetic anhydride was added dropwise at 0 to 3° C. for 1 hour, followed by gradually warming to room temperature and reacting for 9 hours with stirring. After completion of the reaction, the reaction solution was poured into 200 ml of ice water to obtain a treatment solution for formation of iodonium salt. Then, 8.0 g (0.03 mol) of pentafluorobenzenesulphonyl chloride was dissolved in 60 ml of methanol, and 44.0 g (0.072 mol) of an aqueous solution of 15% tetramethylammonium hydroxide was added dropwise thereto at 25 to 35° C. for 30 minutes and reacting at 50° C. for 1 hour with stirring. After completion of the reaction, the reaction solution was concentrated under reduced pressure, and was poured into 40 ml of water to dissolve to obtain an aqueous solution of tetramethylammonium pentafluorobenzenesulfonate. The aqueous solution and 200 ml of dichloromethane were poured into the above-described treatment solution for formation of iodonium salt, followed by reacting at room temperature for 1 hour with stirring. After completion of the reaction, the solution was fractionated, and 200 ml of water was poured into the resulting dichloromethane layer, then sodium hydrocarbonate was added thereto until the solution became neutral, followed by fractionating again. The obtained dichloromethane layer was washed with 200 ml of water and concentrated and evaporated to dryness under reduced pressure, followed by purifying the resulting crude product by a column chromatography to obtain 3.54 g (Yield: 44%) of bis{4-[4-(diphenylsulfonio)phenylthio]phenyl}iodonium tris(pentafluorobenzenesulfonate) as a pale brown glassy substance.

$^1$HNMR (CDCl$_3$) δ ppm: 7.24–7.30 (8H, m, Ar—H), 7.45–7.46 (2H, m, Ar—H), 7.53–7.55 (2H, m, Ar—H), 7.62–7.78 (24H, m, Ar—H) IR (cm$^{-1}$) : 3061, 1642, 1572, 1491, 1466, 1397, 1262, 1225, 1109, 992, 820, 750, 687, 640, 437

Example 9

Photo-curing Experiment 7 g of 3,4-epoxycyclohexylmethyl-3,4-epoxycyclohexylhexanecarboxylate, 3 g of cyclohexeneoxide and 0.20 g of 50% propylene carbonate solution of the compound obtained by Examples 2 to 4, as a cationic type photopolymerization initiator, were mixed. The solution was applied on a glass plate so that a thickness of coating film became 40±10 μm, followed by irradiation with a 50 W/cm high pressure mercury lamp for 60 seconds. Pencil hardness was measured just after the irradiation and one day after the irradiation. As a Comparative Example, photo-curing test of diphenyliodonium hexafluorophosphate was performed at the same time.

TABLE 1

| Cationic type photopolymerization initiator | Just after | 1 Day after |
|---|---|---|
| Compound in Example 2 | 3B | HB |
| Compound in Example 3 | B | H |
| Compound in Example 4 | H | H |
| Diphenyliodonium hexafluorophosphate | HB | HB |

As is clear from Table 1, it was found that use of the hybrid type onium salt of the present invention instead of diphenyliodonium hexafluorophosphate, a known onium salt, as a cationic type photopolymerization initiator showed hardness equivalent to or higher than the known onium salt.

Example 10

A chemically amplified resist composition comprising the following ingredients was prepared.
(1) poly(p-hydroxystyrene/styrene/tert-butyl acrylate) [Mw: 10000, Mw/Mn: 1.70]
 6.0 g
(2) bis{4-[4-(diphenylsulfonio)phenylthio]phenyl}iodonium tris(trifluoromethanesulfonate) [a compound of Example 6]
 0.3 g
(3) organic base
 0.01 g
(4) surfactant
 0.1 g
(5) propylene glycol monomethyl ether acetate
 60.0 g

Example 11

A resist composition was prepared by the same procedure as in Example 10 except that bis{4[4-(diphenylsulfonio)phenylthio]phenyl}iodonium tris(nonafluorobutanesulfonate) [the compound in Example 7] was used (in the same amount) instead of bis{4[4-(diphenylsulfonio)phenylthio]phenyl}iodonium tris(trifluoromethanesulfonate) [the compound in Example 6] used in the composition in Example 10.

Example 12

A resist composition was prepared by the same procedure as in Example 10 except that bis{4-[4-(diphenylsulfonio)phenylthio]phenyl}iodonium tris(pentafluorobenzenesulfonate) [the compound in Example 8] was used (in the same amount) instead of bis{4[4-(diphenylsulfonio)phenylthio]phenyl}iodonium tris(trifluoromethanesulfonate) [the compound in Example 6] used in the composition in Example 10.

Reference Example 1

A resist composition was prepared by the same procedure as in Example 10 except that triphenylsulfonium perfluorobutanesulfonate was used (in the same amount) instead of bis{4[4-(diphenylsulfonio)phenylthio]phenyl}iodonium tris(trifluoromethanesulfonate) [the compound in Example 6] used in the composition in Example 10.

Reference Example 2

A resist composition was prepared by the same procedure as in Example 10 except that diphenyliodonium perfluorobutanesulfonate was used (in the same amount) instead of bis{4[4-(diphenylsulfonio)phenylthio]phenyl}iodonium tris(trifluoromethanesulfonate) [the compound in Example 6] used in the composition in Example 10.

Example 13

A pattern was formed with the use of resist compositions obtained in the above-described Examples 10 to 12 and Reference Examples 1 and 2 after the following process.

Each of the resist compositions was filtered using a 0.1 μm membrane filter, and spin-coated on a silicon substrate, followed by pre-baking at 130° C. for 90 sec. on a hot plate to obtain a resist film of 0.3 μm thick. To transcript a pattern, then irradiation was performed, using an EB direct writing machine having an acceleration voltage of 50 keV (mfd. by Hitachi, Ltd.), followed by baking at 120° C. for 90 sec. on a hot plate and developing using a 2.38% aqueous solution of tetramethylammonium hydroxide to form a pattern on the silicon substrate.

Resist patterns obtained were evaluated as follows.

Namely, sensitivity (Eth) was measured and an exposure dose resolving 0.15 μm line and space at 1:1 was defined as an optimal exposure dose (Eop), and the minimum line width of line and space resolved with this optimal exposure dose was determined as the resolution of resist. Further, shape of the resist pattern was also measured by using a scanning electron microscope. The results are shown in Table 2.

TABLE 2

| | Exposure dose (Eop) μC/cm$^2$ | Resolution μm | Shape of Pattern | Shape of side wall |
|---|---|---|---|---|
| Example 10 [compound in Example 6] | 4.2 | 0.10 | Rectangular | Good |
| Example 11 [compound in Example 7] | 5.4 | 0.10 | Rectangular | Good |

TABLE 2-continued

| | Exposure dose (Eop) μC/cm$^2$ | Resolution μm | Shape of Pattern | Shape of side wall |
|---|---|---|---|---|
| Example 12 [compound in Example 8] | 5.8 | 0.10 | Rectangular | Good |
| Ref. Example 1 (triphenylsulfonium perfluorobutanesulfonate) | 3.4 | 0.15 | Taper | Bad |
| Ref. Example 2 (diphenyliodonium perfluorooctanesulfonate) | 2.2 | 0.15 | Taper | Bad |

As is clear from Table 2, it was found that use of the hybrid type onium salt of the present invention as an acid generator, instead of a known sulfonium salt, triphenylsulfonium nonafluorobutanesulfonate (Reference Example 1), or a known iodonium salt, diphenyliodonium perfluorooctanesulfonate (Reference Example 2), can form a pattern with higher resolution, better shape of more rectangular and better shape of side wall.

INDUSTRIAL APPLICABILITY

Since the hybrid type onium salt of the present invention has a plurality of counter anions in the molecule, the onium salt has advantages such as an improved acid generation efficiency by irradiation with UV, deep UV, KrF excimer laser, ArF excimer laser, F$_2$ excimer laser, electron beams, X-rays or radioactive rays. Therefore, use of the onium salt as a cationic type photopolymerization initiator can form a polymer with high hardness, and use of the onium salt as an acid generator for a chemically amplified resist can prepare a resist composition with high sensitivity.

What is claimed is:

1. A hybrid type onium salt of formula [1]:

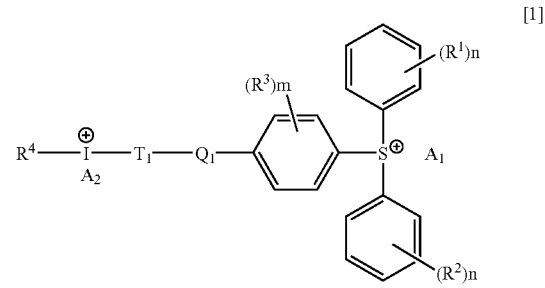

wherein R$^1$ to R$^3$ are each independently a halogen atom, an alkyl group, a haloalkyl group, an aryl group, an alkoxy group, an aryloxy group, an alkylthio group, an arylthio group or an amino group which may be substituted;

Q$_1$ is a direct-linkage, an oxygen atom, a sulfur atom or an alkylene chain having 1 to 6 carton atoms;

T$_1$ is an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted; and R$^4$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, or a group of formula [2]:

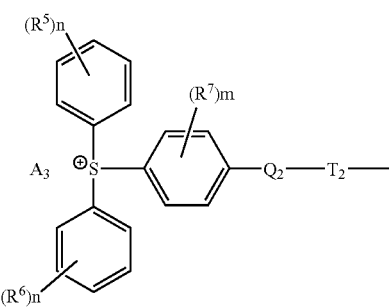

[2]

wherein $R^5$ to $R^7$ are each independently a halogen atom, an alkyl group, a haloalkyl group, an aryl group, an alkoxy group, an aryloxy group, an alkylthio group, an arylthio group or an amino group which may be substituted;

$Q_2$ is a direct-linkage, an oxygen atom, a sulfur atom or an alkylene chain having 1 to 6 carbon atoms;

$T_2$ is an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted;

$A_3$ is a counter anion;

m is an integer of 0 to 4; and each n independently is an integer of 0 to 5;

$A_1$ and $A_2$ are each independently a counter anion; m of formula 1 is an integer of 0 to 4; and each n of formula 1 independently is an integer of 0 to 5.

2. The salt according to claim 1, wherein m and n are 0.

3. The salt according to claim 1, wherein said counter anion of $A_1$ to $A_3$ is a halogen atom or an anion form of formula [7]:

$M^1(R^{11})_4^\ominus$    [7]

wherein $M^1$ is a boron atom or a gallium atom; and $R^{11}$ is an aryl group, which may have a substituent selected from the group consisting of a haloalkyl group having 1 to 4 carbon atoms, a halogen atom, a nitro group and a cyano group, an organic acid or an inorganic acid, or a halogen atom.

4. The salt according to claim 3, wherein said organic acid is a carboxylic acid of formula [8]:

$R^{12}$—COOH    [8]

wherein $R^{12}$ is a hydrogen atom, or an alkyl group, an alkenyl group, an aryl group or an aralkyl group, which may have a halogen atom, or a sulfonic acid of formula [9]:

$R^{13}$—SO$_3$H    [9]

wherein $R^{13}$ is an alkyl group, an aryl group or an aralkyl group, which may have a halogen atom.

5. The salt according to claim 3, wherein said inorganic acid is nitric acid, sulfuric acid, halosulfuric acid, perhalogenic acid or a compound of formula [10]:

HM$^2$F$_l$    [10]

wherein $M^2$ is a metalloid atom or a metal atom; and l is an integer of 4 or 6.

6. The salt according to claim 5, wherein said metalloid atom of $M^2$ is a boron atom, a silicon atom, a phosphorous atom, an arsenic atom or an antimony atom; and said metal atom of $M^2$ is an aluminum atom, a titanium atom, an iron atom, a nickel atom, a gallium atom or a zirconium atom.

7. The salt according to claim 1, wherein said onium salt of formula [1] is one of formula [3]:

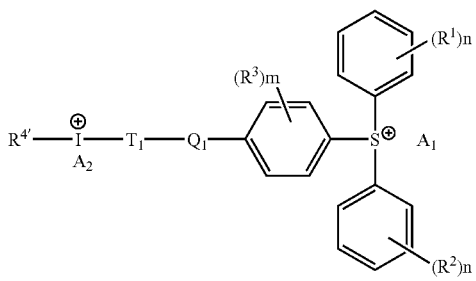

[3]

wherein $R^{4'}$ is an alkyl group, an alkenyl group, an aryl group or an aralkyl group which may have a substituent selected from the group consisting of a halogen atom, an alkyl group, a haloalkyl group, an aryl group, an alkoxy group, an aryloxy group, an alkylthio group, an arylthio group and an amino group which may be substituted; and $R^1$ to $R^3$, $Q_1$, $T_1$, $A_1$, $A_2$, m and n are described in claim 1.

8. The salt according to claim 7, wherein said onium salt of formula [3] is one of formula [4]:

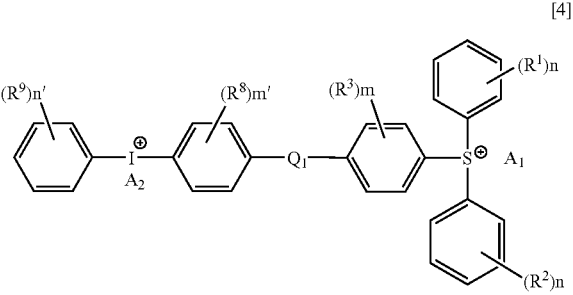

[4]

wherein $R^8$ and $R^9$ are each independently a halogen atom, an alkyl group, a haloalkyl group, an aryl group, an alkoxy group, an aryloxy group, an alkylthio group, an arylthio group or an amino group which may be substituted;

m' is an integer of 0 to 4;

n' is an integer of 0 to 5; and $R^1$ to $R^3$, $Q_1$, $A_1$, $A_2$, m and n are as described in claim 1.

9. The salt according to claim 7, wherein said onium salt of formula [3] is 4-[4-(diphenylsulfonio)phenylthio]phenyl-phenyl iodonium bis(hexafluorophosphate).

10. The salt according to claim 1, wherein said onium salt of formula [1] is one of formula [5]:

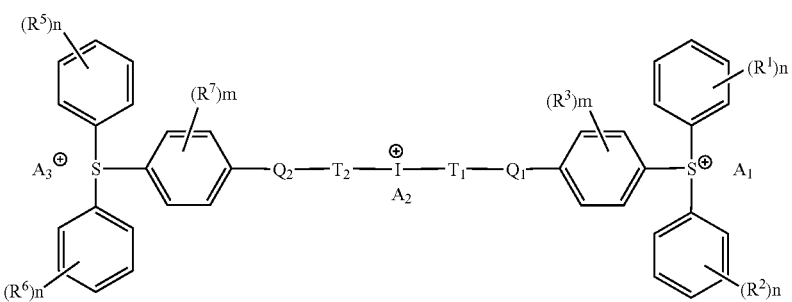

wherein $R^1$ to $R^3$, $R^5$ to $R^7$, $Q_1$, $Q_2$, $T_1$, $T_2$, $A_1$ to $A_3$, m and n are as described in claim 1.

11. The salt according to claim 10, wherein said onium salt of formula [5] is one of formula [6]:

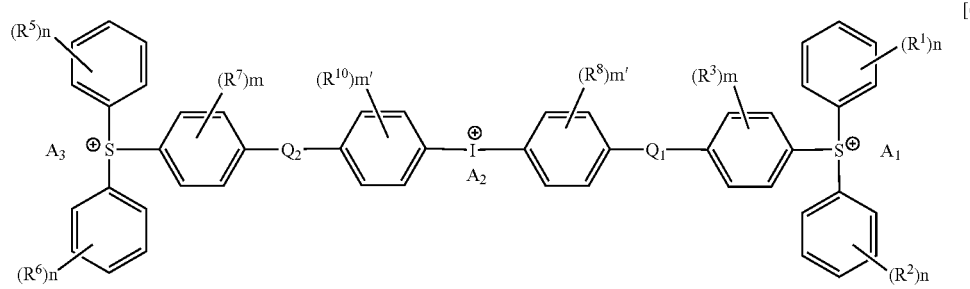

wherein $R^8$ and $R^{10}$ are each independently a halogen atom, an alkyl group, a haloalkyl group, an aryl group, an alkoxy group, an aryloxy group, an alkylthio group, an arylthio group or an amino group which may be substituted;
m' is an integer of 0 to 4; and
$R^1$ to $R^3$, $R^5$ to $R^7$, $Q_1$, $Q_2$, $A_1$ to $A_3$, m and n are as described in claim 1.

12. The salt according to claim 10, wherein said $Q_1$ and $Q_2$ are sulfur atoms.

13. The salt according to claim 12, wherein said onium salt of formula [5] is bis{4-[4-(diphenylsulfonio)phenylthio]phenyl}iodonium tris(hexafluorophosphate), bis{4-[4-(diphenylsulfonio)phenylthio]phenyl}iodonium tris(trifluoromethanesulfonate), bis{4-[4-(diphenylsulfonio)phenylthio]phenyl}iodonium tris(nonafluorobutanesulfonate) or bis{4-[4-(diphenylsulfonio)phenylthio]phenyl}iodonium tris(pentafluorobenzenesulfonate).

14. The salt according to claim 10, wherein said $Q_1$ and $Q_2$ are oxygen atoms.

15. The salt according to claim 14, wherein said onium salt of formula [5] is bis{4-[4-(diphenylsulfonio)phenoxy]phenyl}iodonium tris(hexafluorophosphate).

16. The salt according to claim 10, wherein said $Q_1$ and $Q_2$ are direct-linkages.

17. The salt according to claim 16, wherein said onium salt of formula [5] is bis[4-(diphenylsulfonio)(1,1'-biphenyl)-4'-yl]iodonium tris(hexafluorophosphate).

18. The salt according to claim 10, wherein said alkylene chain of $Q_1$ and $Q_2$ is a methylene group.

19. The salt according to claim 18, wherein said onium salt of formula [5] is bis{4-[4-(diphenylsulfonio)phenylmethyl]phenyl}iodonium tris(hexafluorophosphate).

20. A cationic photopolymerization initiator comprising an onium salt of formula [34]:

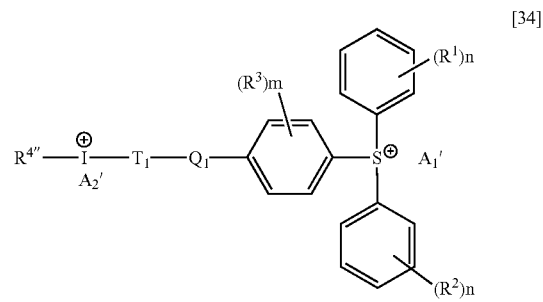

wherein $R^1$ to $R^3$ are each independently a halogen atom, an alkyl group, a haloalkyl group, an aryl group, an alkoxy group, an aryloxy group, an alkylthio group, an arylthio group or an amino group which may be substituted;

$Q_1$ is a direct-linkage, an oxygen atom, a sulfur atom or an alkylene chain having 1 to 6 carbon atoms;

$T_1$ is an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted;

R$^{4''}$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, or a group of formula [35]:

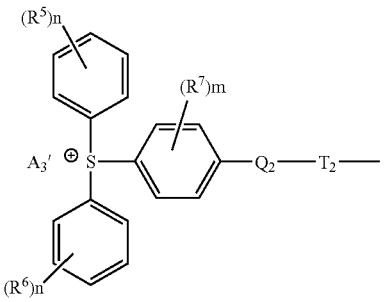

[35]

wherein R$^5$ to R$^7$ are each independently a halogen atom, an alkyl group, a haloalkyl group, an aryl group, an alkoxy group, an aryloxy group, an alkylthio group, an arylthio group or an amino group which may be substituted;

Q$_2$ is a direct-linkage, an oxygen atom, a sulfur atom or an alkylene chain having 1 to 6 carbon atoms;

T$_2$ is an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted;

A$_3$' is a counter anion from of formula [7]:

M$^1$(R$^{11}$)$_4$$^\ominus$ [7]

wherein M$^1$ is a boron atom or a gallium atom; and R$^{11}$ is an aryl group which may have a substituent selected from the group consisting of a haloalkyl group having 1 to 4 carbon atoms, a halogen atom, a nitro group and a cyano group, or an inorganic acid of formula [10]:

HM$^2$F$_l$ [10]

wherein M$^2$ is a metalloid atom or a metal atom; and l is an integer of 4 or 6;

m is an integer of 0 to 4; and each n independently is an integer of 0 to 5;

A$_1$' and A$_2$' are each independently a counter anion form of the formula [7] or an inorganic acid of the formula [10];

m of formula 34 is an integer of 0 to 4; and each n of formula 34 independently is an integer of 0 to 5.

21. The polymerization initiator according to claim 20, wherein said metalloid atom of M$^2$ is a boron atom, a silicon atom, a phosphorous atom, an arsenic atom or an antimony atom; and said metal atom of M$^2$ is an aluminum atom, a titanium atom, an iron atom, a nickel atom, a gallium atom or a zirconium atom.

22. The polymerization initiator according to claim 20, wherein said onium salt of formula [34] is one of formula [36]:

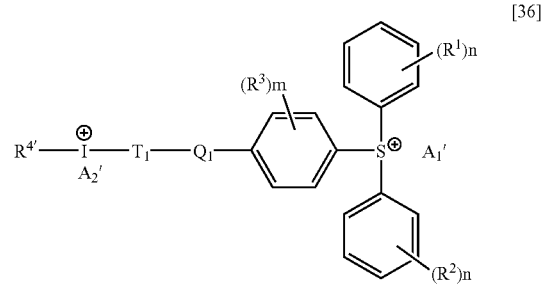

[36]

wherein R$^{4'}$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted; and R$^1$ to R$^3$, Q$_1$, T$_1$, A$_1$', A$_2$', m and n are as described in claim 20.

23. The polymerization initiator according to claim 22, wherein said onium salt of formula [36] is 4-[4-(diphenylsulfonio)phenylthio]phenyl-phenyl iodonium bis(hexafluorophosphate).

24. A polymerization initiator according to claim 20, wherein said onium salt of formula [34] is one of formula [38]:

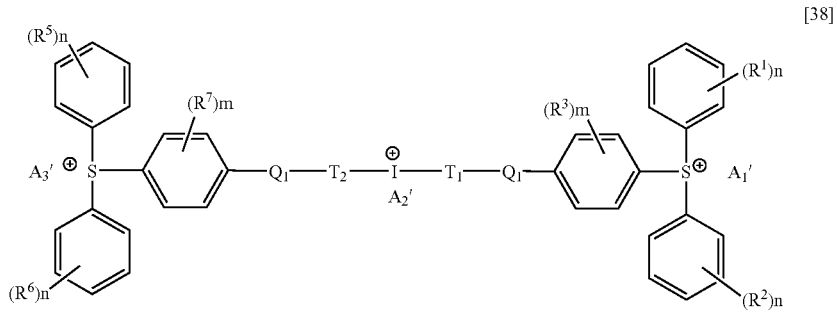

[38]

wherein R$^1$ to R$^3$, R$^5$ to R$^7$, Q$_1$, Q$_2$, T$_1$, T$_2$, A$_1$' to A$_3$', m and n are as described in claim 20.

25. The polymerization initiator according to claim 24, wherein said onium salt of formula [38] is bis{4-[4-(diphenylsulfonio)phenylthio]phenyl}iodonium tris(hexafluorophosphate), bis{4-[4-(diphenylsulfonio)phenoxy]phenyl}iodonium tris(hexafluorophosphate), bis[4-(diphenylsulfonio)(1,1'-biphenyl)-4'-yl]iodonium tris(hexafluorophosphate) or bis{4-[4-(diphenylsulfonio)phenylmethyl]phenyl}iodonium tris(hexafluorophosphate).

26. A method for polymerizing an α, β-ethylenically unsaturated monomer, which comprises using the polymerization initiator in claim 20.

27. A method for polymerizing a vinyl ether monomer, which comprises using the polymerization initiator in claim 20.

28. A method for polymerizing an epoxy monomer, which comprises using the polymerization initiator in claim 20.

29. An acid generator for a resist, comprising an onium salt of formula [40]:

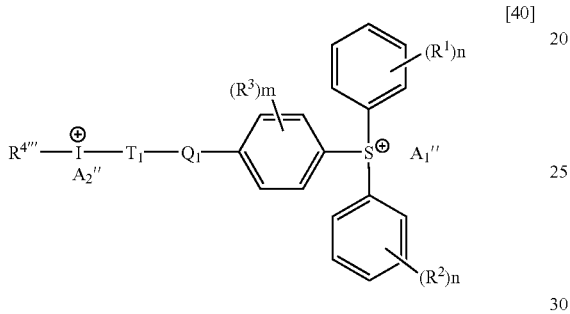

[40]

wherein $R^1$ to $R^3$ are each independently a halogen atom, an alkyl group, a haloalkyl group, an aryl group, an alkoxy group, an aryloxy group, an alkylthio group, an arylthio group or an amino group which may be substituted;

$Q_1$ is a direct-linkage, an oxygen atom, a sulfur atom or an alkylene chain having 1 to 6 carbon atoms;

$T_1$ is an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted;

$R^{4'''}$ is an alkyl group, an alkenyl group, an aryl group or an aralkyl group, which may have a substituent selected from the group consisting of a halogen atom, an alkyl group, a haloalkyl group, an aryl group, an alkoxy group, an aryloxy group, an alkylthio group, an arylthio group and an amino group which may be substituted, or a group of formula [41]:

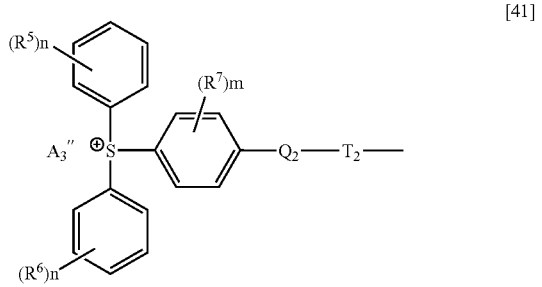

[41]

wherein $R^5$ to $R^7$ are each independently a halogen atom, an alkyl group, a haloalkyl group, an aryl group, an alkoxy group, an aryloxy group, an alkylthio group, an arylthio group or an amino group which may be substituted;

$Q_2$ is a direct-linkage, an oxygen atom, a sulfur atom or an alkylene chain having 1 to 6 carbon atoms;

$T_2$ is an alkylene group or an arylene group, which may have a substituent selected from the group consisting of a halogen atom, an alkyl group, a haloalkyl group, an aryl group, an alkoxy group, an aryloxy group, an alkylthio group, an arylthio group and an amino group which may be substituted;

$A_3''$ is an anion form of formula [7]:

$$M^1(R^{11})_4^{\ominus} \quad [7]$$

wherein $M^1$ is a boron atom or a gallium atom;

$R^{11}$ is an aryl group which may have a substituent selected from the group consisting of a haloalkyl group having 1 to 4 carbon atoms, a halogen atom, a nitro group and a cyano group, an organic acid or an inorganic acid;

m is an integer of 0 to 4; and each n independently is an integer of 0 to 5;

$A_1''$ and $A_2''$ are each independently an anion form of formula [7], an organic acid or an inorganic acid;

m is an integer of 0 to 4; and each n independently is an integer of 0 to 5.

30. The acid generator according to claim 29, wherein said anion form of an organic acid of $A_1''$ to $A_3''$ is an anion form of a carboxylic acid of formula [8]:

$$R^{12}-COOH \quad [8]$$

wherein $R^{12}$ is a hydrogen atom, or an alkyl group, an alkenyl group, an aryl group or an aralkyl group, which may have a halogen atom, or a sulfonic acid of formula [9]:

$$R^{13}-SO_3H \quad [9]$$

wherein $R^{13}$ is an alkyl group, an aryl group or an aralkyl group, which may have a halogen atom.

31. The acid generator according to claim 29, wherein said anion derived from an inorganic acid of $A_1''$ to $A_3''$ is an anion form of nitric acid, sulfuric acid, halosulfuric acid, perhalogenic acid, or a compound of formula [10]:

$$HM^2F_l \quad [10]$$

wherein $M^2$ is a metalloid atom or a metal atom; and l is an integer of 4 or 6.

32. The acid generator according to claim 29, wherein said onium salt of formula [40] is bis{4-[4-(diphenylsulfonio)phenylthio]phenyl}iodonium tris(hexafluorophosphate), bis{4-[4-(diphenylsulfonio)phenylthio]phenyl}iodonium tris(trifluoromethanesulfonate), bis{4-[4-(diphenylsulfonio)phenylthio]phenyl}iodonium tris(nonafluorobutanesulfonate), bis{4-[4-(diphenylsulfonio)phenylthio]phenyl}iodonium tris(pentafluorobenzenesulfonate), bis{4-[4-(diphenylsulfonio)phenoxy]phenyl}iodonium tris(hexafluorophosphate), bis[4-(diphenylsulfonio)(1,1'-biphenyl)-4'-yl]iodonium tris(hexafluorophosphate) or bis{4-[4-(diphenylsulfonio)phenylmethyl]phenyl}iodonium tris(hexafluorophosphate).

* * * * *